(12) United States Patent
Ishikawa et al.

(10) Patent No.: US 10,034,851 B2
(45) Date of Patent: Jul. 31, 2018

(54) METAL-SALEN COMPLEX COMPOUND, LOCAL ANESTHETIC AND ANTINEOPLASTIC DRUG

(71) Applicants: IHI Corporation, Tokyo (JP); Yoshihiro Ishikawa, Tokyo (JP)

(72) Inventors: Yoshihiro Ishikawa, Tokyo (JP); Haruki Eguchi, Tokyo (JP)

(73) Assignees: IHI Corporation, Tokyo (JP); Yoshihiro Ishikawa, Tokyo (JP)

( * ) Notice: Subject to any disclaimer, the term of this patent is extended or adjusted under 35 U.S.C. 154(b) by 18 days.

(21) Appl. No.: 15/045,511

(22) Filed: Feb. 17, 2016

(65) Prior Publication Data

US 2016/0263074 A1    Sep. 15, 2016

Related U.S. Application Data

(63) Continuation of application No. 14/126,205, filed as application No. PCT/JP2012/062016 on May 10, 2012, now abandoned.

(30) Foreign Application Priority Data

Jun. 13, 2011 (JP) ................................ 2011-131239

(51) Int. Cl.

| | |
|---|---|
| A61K 31/295 | (2006.01) |
| A61K 31/555 | (2006.01) |
| A61K 9/06 | (2006.01) |
| A61M 35/00 | (2006.01) |
| A61M 19/00 | (2006.01) |
| C07F 15/02 | (2006.01) |
| A61K 31/28 | (2006.01) |
| A61K 31/566 | (2006.01) |
| A61K 31/661 | (2006.01) |
| A61K 31/7135 | (2006.01) |
| A61K 38/12 | (2006.01) |
| A61K 47/48 | (2006.01) |
| A61K 9/00 | (2006.01) |
| A61F 7/00 | (2006.01) |

(52) U.S. Cl.
CPC .......... *A61K 31/295* (2013.01); *A61K 9/0014* (2013.01); *A61K 9/06* (2013.01); *A61K 31/28* (2013.01); *A61K 31/555* (2013.01); *A61K 31/566* (2013.01); *A61K 31/661* (2013.01); *A61K 31/7135* (2013.01); *A61K 38/12* (2013.01); *A61K 47/48023* (2013.01); *A61K 47/4823* (2013.01); *A61K 47/48038* (2013.01); *A61K 47/48061* (2013.01); *A61K 47/48076* (2013.01); *A61K 47/48107* (2013.01); *A61K 47/48123* (2013.01); *A61K 47/48153* (2013.01); *A61K 47/48238* (2013.01); *A61K 47/48246* (2013.01); *A61M 19/00* (2013.01); *A61M 35/00* (2013.01); *C07F 15/025* (2013.01); *A61F 2007/009* (2013.01)

(58) Field of Classification Search
CPC ...... A61K 31/295; A61K 9/06; A61K 31/555; A61M 19/00; A61M 35/00; A61F 2007/009
USPC .................................................. 556/1; 540/1
See application file for complete search history.

(56) References Cited

U.S. PATENT DOCUMENTS

| | | | |
|---|---|---|---|
| 5,403,834 A | 4/1995 | Malfroy-Camine | |
| 5,549,915 A | 8/1996 | Volkonsky et al. | |
| 5,696,109 A | 12/1997 | Malfroy-Camine | |
| 6,046,188 A | 4/2000 | Malfroy-Camine | |
| 7,582,786 B2 * | 9/2009 | Malfroy-Camine | .. C07F 13/005 556/34 |
| 2005/0096260 A1 | 5/2005 | Ueno et al. | |
| 2009/0169484 A1 | 7/2009 | Eguchi et al. | |
| 2009/0311163 A1 | 12/2009 | Eguchi et al. | |
| 2012/0029167 A1 | 2/2012 | Ishikawa et al. | |
| 2014/0046021 A1 | 2/2014 | Ishikawa | |
| 2014/0206635 A1 | 7/2014 | Ishikawa et al. | |

FOREIGN PATENT DOCUMENTS

| | | |
|---|---|---|
| EP | 2357166 A1 | 8/2011 |
| EP | 2657233 A1 | 10/2013 |
| EP | 2682384 A1 | 1/2014 |
| JP | H08504211 A | 5/1996 |
| JP | H11507646 A | 7/1999 |
| JP | 2001010978 A | 1/2001 |
| JP | 2009-173631 A | 8/2009 |
| JP | 2009-274962 A | 11/2009 |
| JP | 2010-43125 A | 2/2010 |
| JP | 2010222264 A | 10/2010 |
| JP | 2012167067 A | 9/2012 |
| WO | 1994013300 A1 | 6/1994 |
| WO | 1996040148 A1 | 12/1996 |
| WO | 2001080849 A1 | 11/2001 |
| WO | 03035078 A1 | 1/2003 |
| WO | 2008001851 A1 | 1/2008 |
| WO | 2010/58280 A1 | 5/2010 |

OTHER PUBLICATIONS

Herchel et al. Novel 1D chain Fe(III)-salen-like complexes involving anionic heterocyclic N-donor ligands. Synthesis, X-ray structure, magnetic, 57Fe Mossbauer, and biological activity studies. Dalton Trans., 9870-9880, 2009. (Year: 2009).*

(Continued)

*Primary Examiner* — Yih-Horng Shiao
(74) *Attorney, Agent, or Firm* — Brundidge & Stanger, P.C.

(57) ABSTRACT

A metal-salen complex compound, which exhibits excellent noninvasiveness and can be efficiently transferred to an affected site, a local anesthetic containing this metal-salen complex compound, and an antineoplastic drug containing this metal-salen complex compound are provided. Regarding the metal-salen complex compound, a metal atom part in each of two molecules of a metal-salen complex or a derivative of the metal-salen complex is dimerized via water, and the metal-salen complex compound is mixed with a base to produce an ointment.

6 Claims, 18 Drawing Sheets

(56) References Cited

OTHER PUBLICATIONS

Muramatsu et al. Superoxide Dismutase in SAS Human Tongue Carcinoma Cell Line Is a Factor Defining Invasiveness and Cell Motility. Cancer Research 55, 6210-6214, Dec. 15, 1995. (Year: 1995).*
The Pharmaceutical Society of Japan, Dispensing Guidelines, 12th Revision, Yakuji Nippo Limited, 2006, pp. 135-138.
Japanese Office Action dated May 19, 2015.
D. Delledonne et al, "Oxidative carbonylation of Methanol to dimethyl carbonate (DMC): a new catalytic system" Journal of Organometallic Chemistry, 1995, vol. 488, Nos. 1-2, p. C15-C19.
JP Office Action dated Dec. 2, 2014.
Russian Office Action dated Mar. 3, 2015.
D. A. Kharkevich, "Pharmacology", Third Edition, revised and supplemented, Allowed by the Principal Administration of Educational Institutions under the Ministry of Public Health of the USSR, as a textbook for medical students, Moscow, Meditsina 1980, 2 pages.
V. G. Belikov, "Pharmaceutical Chemistry", Moscow, Vysshaya shkola, 1993, pp. 43-47.
RU Office Action dated Jan. 27, 2016 directed to the RU counterpart application No. 2013156414, and its English translation, pp. 1-7.
Hiizu Iwamura "Design of Organic Ferromagnets" Feb. 1989, pp. 76-88 (cited in the original specification) (non-patent literature).
Kristy Cochran et al. "cis-Diamminodlchloronickel and Its Interaction With Guanine and Guanine-Cytosine Base Pair" vol. 13, No. 2, Apr. 2002, pp. 133-140 (cited un the original specification) (non-patent literature).
International Search Report issued in corresponding application No. PCT/JP2012/062016 dated Aug. 7, 2012.
International Search Authority issued in corresponding application No. PCT/JP2012/062016 dated Aug. 7, 2012.

* cited by examiner

IMAGES TAKEN FROM
THIS END TO THE OTHER END

Saline  SC  SC+Mag

METAL-SALEN COMPLEX COMPOUND, LOCAL ANESTHETIC AND ANTINEOPLASTIC DRUG

CROSS REFERENCED TO RELATED APPLICATION

The present application is a continuation of application Ser. No. 14/126,205, filed Mar. 31, 2014, which claims priority from PCT/JP2012/062016, filed May 10, 2012, the contents of which are incorporated herein by reference.

TECHNICAL FIELD

The present invention relates to a metal-salen complex compound and to a metal-salen complex compound, which is self-magnetic and can be applied to ointment compositions, a local anesthetic containing this metal-salen complex compound, and an antineoplastic drug containing this metal-salen complex compound.

BACKGROUND ART

Generally, when a drug is administered to a living body, it reaches an affected site and exerts its pharmacological effects at that affected site, thereby exerting its therapeutic effects. On the other hand, even if the drug reaches tissue other than the affected site (that is, normal tissue), it will not be therapeutic. Therefore, how to guide the drug to the affected site is important.

A technique to guide the drug to the affected site is called drug delivery, which has been actively studied and developed recently. This drug delivery has at least two advantages. One advantage is that a sufficiently high drug concentration can be obtained at the affected site tissue. Pharmacological effects will not be seen unless the drug concentration at the affected site is a constant value or more. The sufficient therapeutic effects cannot be expected if the drug concentration is low. The second advantage is that the drug is guided to only the affected site tissue and, therefore, adverse reactions to the normal tissue can be inhibited.

Such drug delivery is most effective for 185 a cancer treatment by antitumor agents. Most antitumor agents inhibit the cell growth of cancer cells which divide actively, so that the antitumor agents will also inhibit the cell growth of even the normal tissue in which cells divide actively, such as bone marrow, hair roots, or alimentary canal mucosa. Therefore, cancer patients to whom the antitumor agents are administered suffer adverse reactions such as anemia, hair loss, and vomiting. Since such adverse reactions impose heavy burdens on the patients, the dosage needs to be limited, thereby causing a problem of incapability to sufficiently obtain the pharmacological effects of the antitumor agents.

Alkyl antineoplastic drugs among such anti-tumor agents (antineoplastic drugs) are a generic term for antitumor agents having the ability to combine an alkyl group ($-CH_2-CH_2-$) with, for example, a nucleic acid protein and have the effects of alkylating DNA and inhibiting DNA replication, causing cell death. These effects work regardless of cell cycles, also works on cells of the $G_0$ period, has a strong effect on cells which grow actively, and tends to damage, for example, bone marrow, alimentary canal mucosa, germ cells, or hair roots.

Moreover, antimetabolite antineoplastic drugs are compounds having structures similar to those of nucleic acids or metabolites in a protein synthesis process, impairs cells by, for example, inhibiting synthesis of the nucleic acids, and specifically acts on cells of a mitotic period.

Antitumor antibiotics are chemical substances produced by microorganisms, have actions such as DNA synthesis inhibition and DNA strand breaking, and exhibit antitumor activity.

Also, microtubule inhibitors have antitumor effects by directly acting on microtubules that serve important roles to maintain normal functions of cells, for example, by forming spindles during cell division, locating cell organelles, and transporting substances. The microtubule inhibitors act on cells, which divide actively, and nerve cells.

Moreover, platinum preparations inhibit DNA synthesis by forming DNA strands, interchain bonds, or DNA protein bonds. Cisplatin is a representative drug, but it causes severe nephropathia and requires a large amount of fluid replacement.

Furthermore, parahormone antineoplastic drugs are effective against hormone-dependent tumors. Female hormones or anti-androgen drugs are administered to an androgen-dependent prostatic cancer.

Molecular targeted drugs are used for a treatment targeted at molecules that correspond to molecular biological characters specific to respective malignant tumors.

Moreover, topoisomerase inhibitors are enzymes for temporarily generating breaks in DNA and changing the number of tangles of DNA strands. A topoisomerase inhibitor I is an enzyme that generates breaks in one strand of a circular DNA, lets the other strand pass, and then closes the breaks; and a topoisomerase inhibitor II temporarily breaks both the two strands of the circular DNA, lets other two DNA strands pass between the former two strands, and reconnects the broken strands.

Furthermore, nonspecific immunopotentiators inhibit an increase of cancer cells by activating the immune system.

Topical anesthetics also have the advantage of drug delivery. The topical anesthetics are used to treat topical itches and pains of, for example, mucosa or skin caused by hemorrhoidal disease, stomatitis, gum disease, cavities, tooth extraction, or operations. Lidocaine (product name: xylocaine) is known as a representative topical anesthetic; however, this lidocaine is faster-acting, but has an antiarrhythmic effect. Furthermore, if lidocaine which is an anesthetic is injected into the spinal fluid when giving spinal anesthesia, lidocaine will spread through the spinal fluid; and in a worst-case scenario, there is fear that lidocaine might reach a cervical part of the spinal cord and thereby cause a respiratory function to stop and bring about critical adverse effects.

An example of a specific method for the drug delivery is the use of a carrier. This is to load the carrier, which tends to concentrate on the affected site, with the drug and have the carrier carry the drug to the affected site. A promising candidate of the carrier is a magnetic substance and there is a suggested method of attaching the carrier, which is the magnetic substance, to the drug and allowing the carrier to be accumulated at the affected site by a magnetic field (see, for example, Patent Literature 1).

However, when using the magnetic substance carrier as the carrier, it is difficult to aurally administer the magnetic substance carrier, molecules of the carrier are generally giant, and there are technical problems about binding strength and affinity between the carrier and the drug molecules; and because of the above-described reasons, it has been difficult to achieve the practical use of the magnetic substance carrier.

Therefore, a topical anesthetic is introduced in which side chains for giving positive or negative spin charge density are bonded to a basic skeleton of an organic compound, and which has suitability as a whole insofar as the topical anesthetic is guided, by means of magnetism by an external magnetic field; and if the topical anesthetic is applied to a human body or an animal, it is retained in an area where a magnetic field is applied topically by the magnetic field outside the body and the medicinal effects that the topical anesthetic originally has are exerted on the area. The above-mentioned technique uses the iron-salen complex as an example of such a drug (see Patent Literature 2).

Furthermore, a review article is introduced about an organic magnetic substance which creates magnets from high polymer materials by means of synthesis of "high-spin molecules" with more parallel spins than conventional metal magnetic substances (for example, see Patent Literature 3).

Furthermore, a technique that substitutes platinum contained in cisplatin with another element is also introduced (for example, see Patent Literature 4).

CITATION LIST

Patent Literature

[Patent Literature 1] Japanese Patent Application Laid-Open (Kokai) Publication No. 2001-10978
[Patent Literature 2] WO2008/001851
[Non Patent Literature 1] Hiizu Iwamura, "Molecular Design Aimed at Organic Ferromagnetic Substances," February 1989 issue, p.p. 76-88
[Non Patent Literature 2] Krsity Cochran et al., Structural Chemistry, 13(2002), p.p. 133-140

SUMMARY OF INVENTION

Technical Problem

However, development of, for example, drugs and drug delivery systems capable of efficiently transferring more excellent invasive medicines to an affected site is anticipated for treatments which relatively put a strain on patients as in, for example, treatments for tongue cancers, postorbital part tissues, or the like.

The present invention was devised in light of such circumstances and it is an object of the invention to provide a metal-salen complex compound, which exhibits excellent noninvasiveness and can be efficiently transferred to an affected site, a local anesthetic containing this metal-salen complex compound, and an antineoplastic drug containing this metal-salen complex compound.

Solution to Problem

In order to achieve the above-described object, the present invention provides a metal-salen complex compound in which a metal atom part in each of multiple molecules of a metal-salen complex or a derivative of the metal-salen complex is multimerized via water, and which is mixed with a base to produce an ointment.

Moreover, regarding the metal-salen complex compound according to the present invention, the multiple molecules should more preferably be two molecules and the metal atom part of each of the two molecules should more preferably be dimerized via water.

Since this metal-salen complex compound can be mixed with the base to produce the ointment, it can be administered as the ointment to the affected site. Therefore, the metal-salen complex compound exhibits excellent noninvasiveness and can be transferred efficiently to the affected site.

Incidentally, the "ointment" according to the present invention includes, in addition to, for example, ointments using oleaginous bases, creams using emulsion bases as specified by Japanese Pharmacopoeia. The "base" used to produce the ointment serves to adhere to the skin and make active ingredients stay on the skin for a long time and the base which can be easily applied, has no irritating effect on the skin, and does not affect stability of the active ingredients is required.

Moreover, the metal-salen complex compound according to the present invention can be applied to, for example, a tongue, gums, and the inside of cheeks by being mixed with a base which can be used in the oral cavity.

Examples of such a base can include hydrophobic bases (oleaginous bases), hydrophilic bases (emulsion bases, water-soluble bases, lyophobic bases), special formulations (such as liniments, pastes (pastas), plasters, lotions, and sprays), oral ointments, and ophthalmic ointments. More specifically, for example, ointment bases such as Vaseline (yellow Vaseline, hydrophilic Vaseline, and white Vaseline), Kenalog, liquid paraffin, castor oil polyethoxylated hydrogenated, macrogol, and gelled hydrocarbon.

A preferred embodiment of the present invention is a self-magnetic metal-salen complex represented by the following chemical formulas (I), (II), (III) and its derivatives.

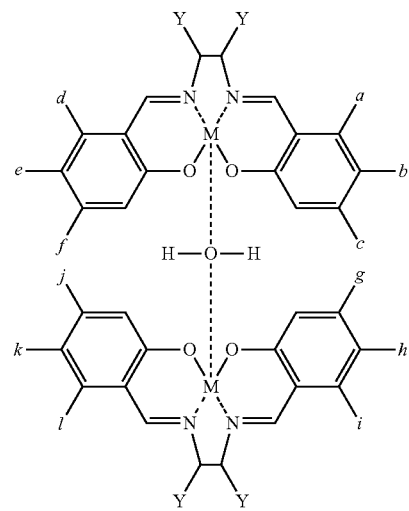

Formula (I)

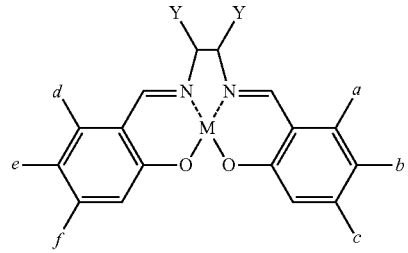

Formula (II)

-continued

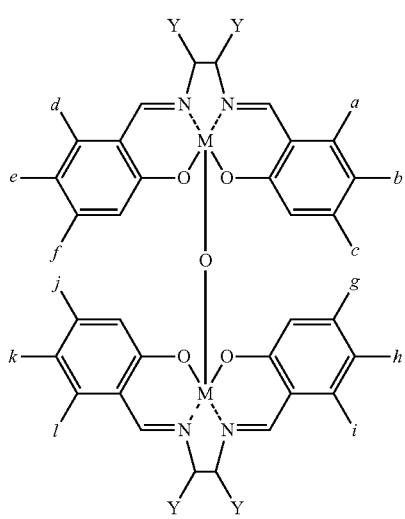

Formula (III)

However, regarding all Formulas (I), (II), and (III), M represents Fe (iron), Cr (chromium), Mn (manganese), Co (cobalt), Ni (nickel), Mo (molybdenum), Ru (rubidium), Rh (rhodium), Pd (palladium), W (tungsten), Re (rhenium), Os (osmium), Ir (iridium), Pt (platinum), Nd (niobium), Sm (samarium), Eu (europium) or Gd (gadolinium) and each of a to f and Y is hydrogen (where M is Fe, excluding a case where all of a to f and Y are hydrogens) or any one of the following (1) to (7):

—CO₂Me (1)

—CO(OCH₂CH₂)₂OCH₃ (2)

(3)

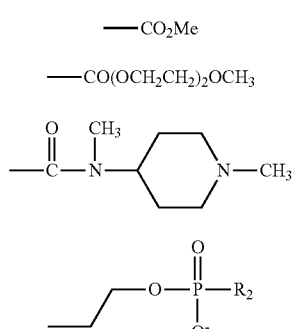

(4)

(where R₂ represents a plurality of nucleic acids which are combined together and are formed of adenine, guanine, thymine, cytosine, or uracil);

(5) —NHCOH, —NH₂, —NHR₁, or, —NR₁R₂

(where R₁ and R₂ are alkyl or alkane with the same carbon number or the carbon number from 1 to 6);

(6) —NHR₃—, —NHCOR₃, or, —R₃

(where R₃ represents a substituent bound as a result of desorption of a functional group such as hydrogen or a hydroxyl group); and (7) halogen atoms such as chlorine, bromine, or fluorine.

Moreover, charge transfer of R₃ should preferably be less than 0.5 electrons (e).

Furthermore, R₃ can be any one of compounds represented by the following formulas (1) to (27).

(1) Ibuprofen piconol, phenylpropionic acid analgesic/anti-inflammatory

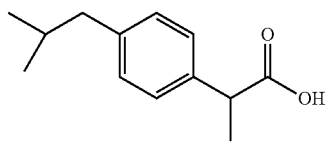

ibuprofen (2) Mefenamic, anthranilic-acid anti-inflammatory analgesic

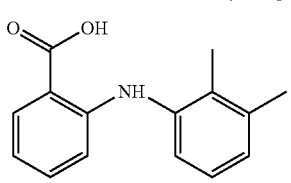

mefenamic acid (3) Drug for treating hyperlipemia

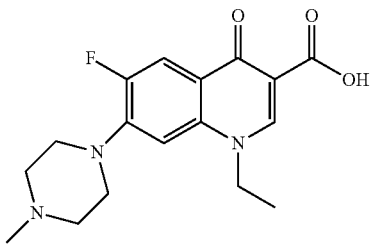

pefloxacin (4) Antibacterial

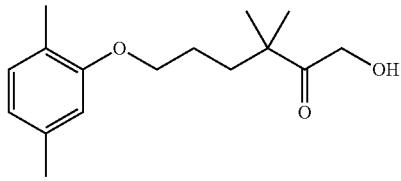

gemfibrozil (5) Fluorochrome (rhodamine)

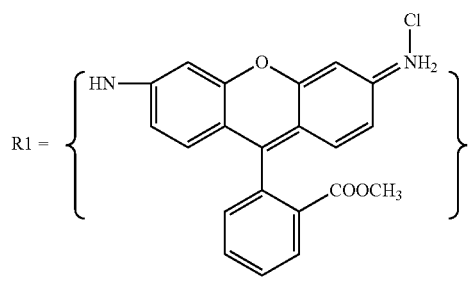

(6) Hormone (estrogen)

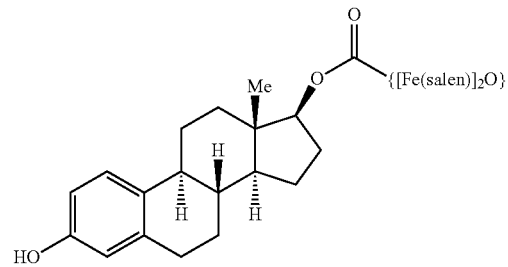

(7) Hormone (estrogen)
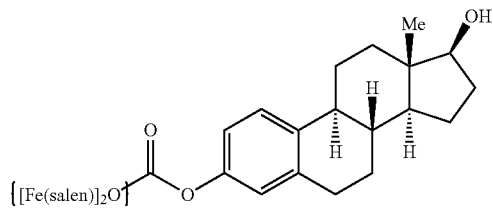
(8) Taxol (paclitaxel)
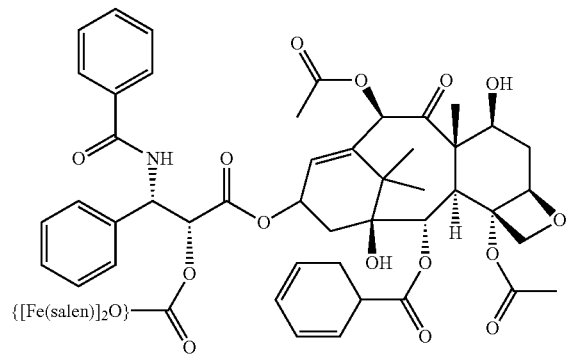
(9) Amino acid (glycine)
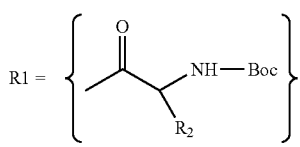
(10) Amino acid (alanine)
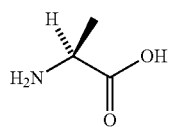
(11) Amino acid (arginine)
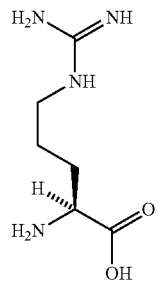
(12) Amino acid (asparagine)
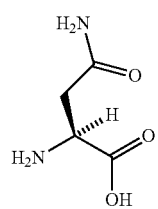
(13) Amino acid (aspartic acid)
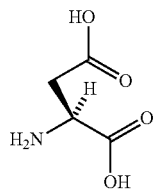
(14) Amino acid (cystenine)
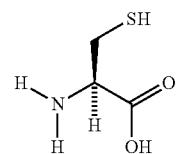
(15) Amino acid (glutamic acid)
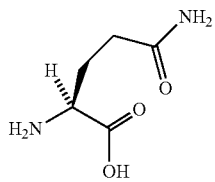
(16) Amino acid (histidine)
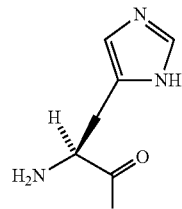
(17) Amino acid (isoleucine)
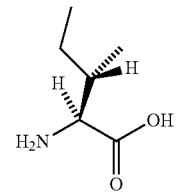
(18) Amino acid (leucine)
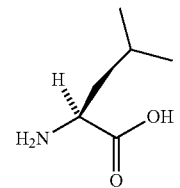
(19) Amino acid (lysine)
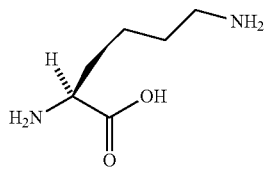

(20) Amino acid (methionine)

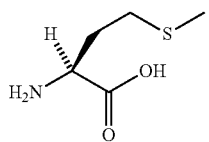

(21) Amino acid (phynelalanine)

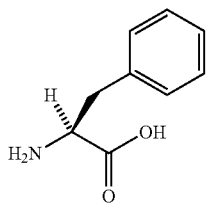

(22) Amino acid (proline)

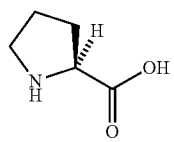

(23) Amino acid (serine)

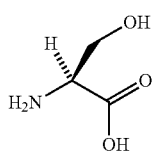

(24) Amino acid (threonine)

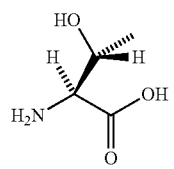

(25) Amino acid (tryptophan)

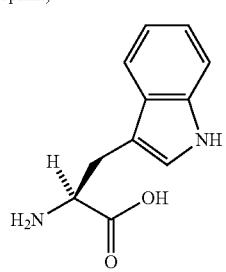

(26) Amino acid (tyrosine)

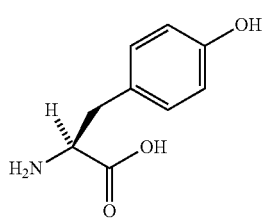

(27) Amino acid (valine)

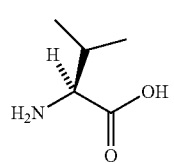

Furthermore, the present invention provides a local anesthetic having a self-magnetic metal-salen complex compound wherein $R_3$ is a substituent represented by any of the following formulas (28) to (38) obtained as a result of desorption of hydrogen from a compound which has a methyl group and whose charge transfer is less than 0.5 electors (e).

(28) General name: lidocaine

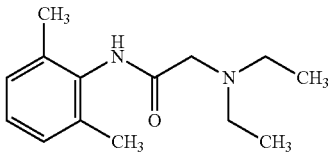

lidocaine

(29) General name: ethyl aminobenzoic acid

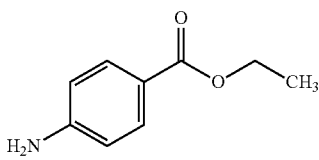

(30) General name: oxybuprocaine hydrochloride

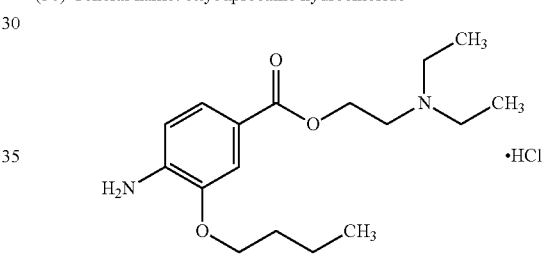

(31) General name: oxethazaine

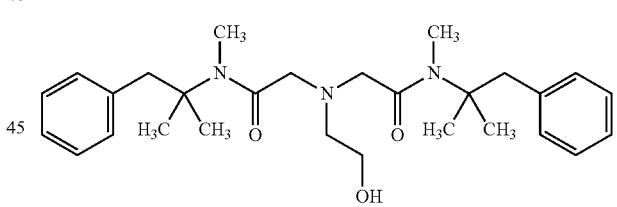

(32) General name: dibucaine

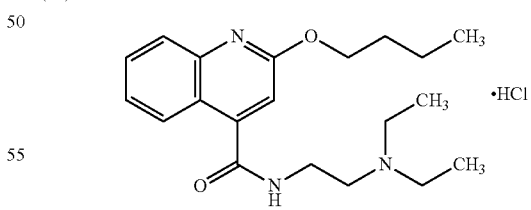

(33) General name: ethylpiperidinoacetylaminobenzoate

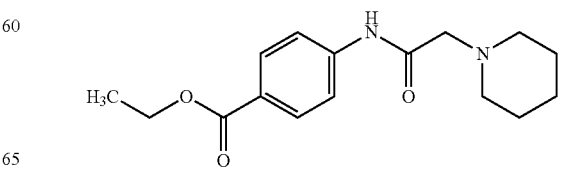

(34) General name: procaine

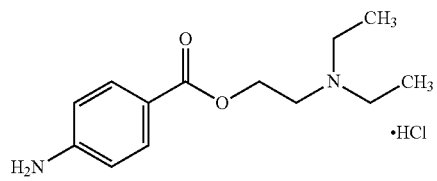

(35) General name: mepivacaine

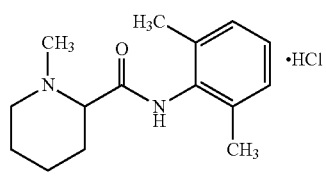

(36) General name: p-butylaminobenzoyldiethylaminoethanol hydrochloride

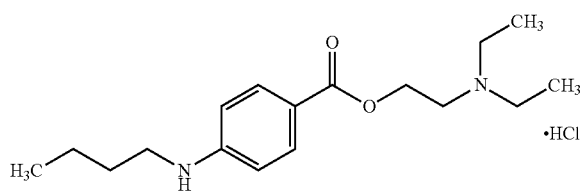

(37) General name: bupivacaine hydrochloride

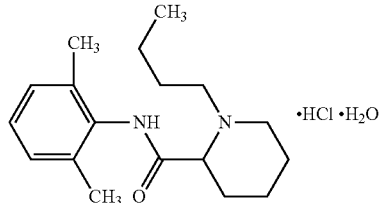

(38) General name: ropivacaine hydrochloride hydrate

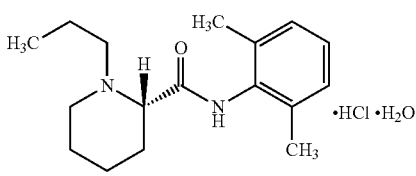

Furthermore, the present invention provides an antineoplastic drug having a self-magnetic metal-salen complex compound wherein $R_3$ is any one of compounds represented by the following formulas (39) to (103), which combines with a main skeleton of the compound of the above formula I via a linking group part obtained as a result of desorption of hydrogen (however, with the compound (83), a cyano group (—CN) is the linking group).

(39) General name: ifosfamide, alkyl antineoplastic drug formula3

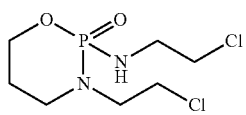

(40) General name: cyclophosphamide, alkyl antineoplastic drug formula4

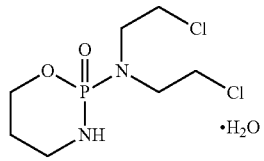

(41) General name: dacarbazine, alkyl antineoplastic drug formula5

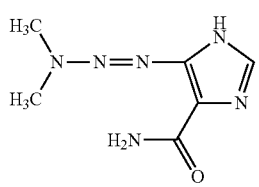

(42) General name: busulfan alkyl antineoplastic drug formula6

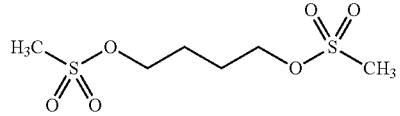

(43) General name: melphalan, alkyl antineoplastic drug formula7

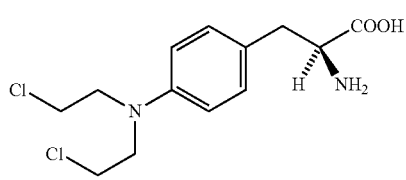

(44) General name: ranimustine, alkyl antineoplastic drug formula8

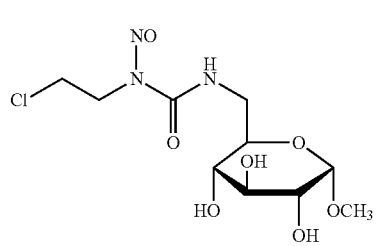

-continued

(45) General name: estramustine sodium phosphate, alkyl antineoplastic drug formula9

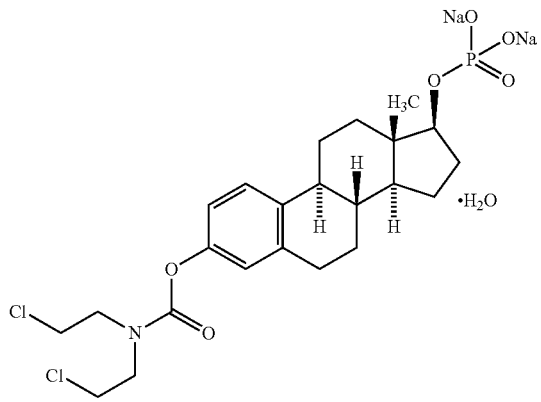

(46) General name: nimustine hydrochloride, alkyl antineoplastic drug formula10

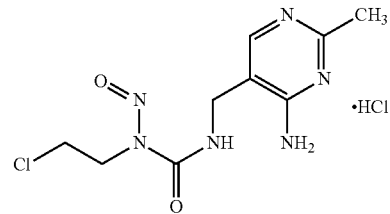

(47) General name: enocitabine, antimetabolite antineoplastic drug formula11

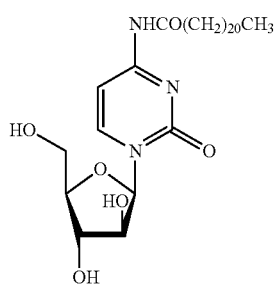

(48) General name: capecitabine, antimetabolite antineoplastic drug formula12

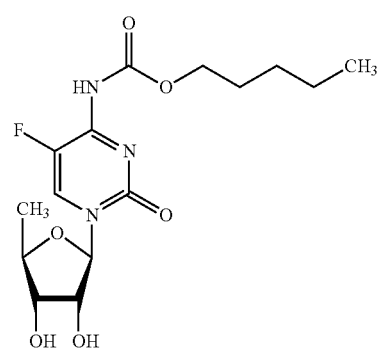

(49) General name: carmofur, antimetabolite antineoplastic drug formula13

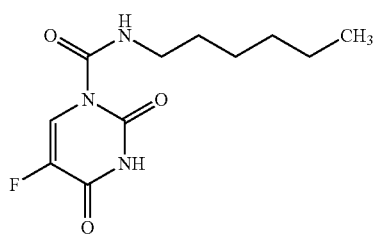

(50) General name: gimeracil, antimetabolite antineoplastic drug formula14

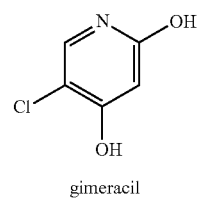

gimeracil

(51) General name: oteracil potassium, antimetabolite antineoplastic drug formula15

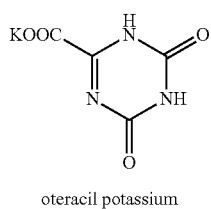

oteracil potassium

(52) General name: cytarabine, antimetabolite antineoplastic drug formula16

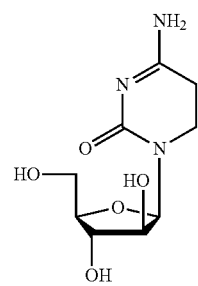

(53) General name: cytarabine ocfosfate, antimetabolite antineoplastic drug formula17

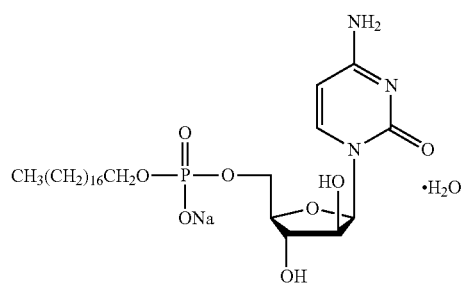

(54) General name: tegafur, antimetabolite antineoplastic drug formula18

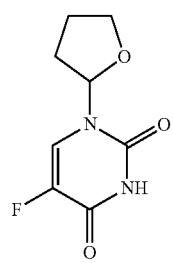

(55) General name: doxifluridine, antimetabolite antineoplastic drug formula19

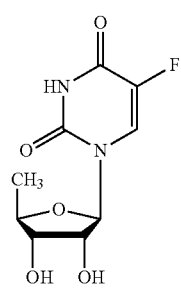

(56) General name: hydroxycarbamide, antimetabolite antineoplastic drug formula20

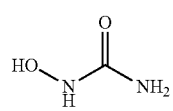

(57) General name: fluorouracil, antimetabolite antineoplastic drug formula 21

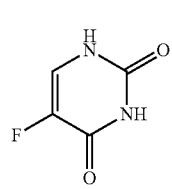

(58) General name: mercaptopurine hydrate, antimetabolite antineoplastic drug formula 22

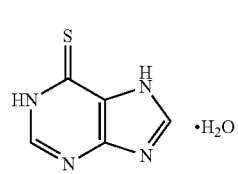

(59) General name: fludarabine phosphate, antimetabolite antineoplastic drug forumula23

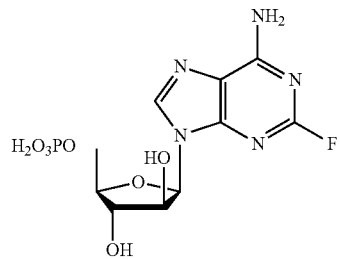

(60) General name: gemcitabine hydrochloride, antimetabolite antineoplastic drug formula24

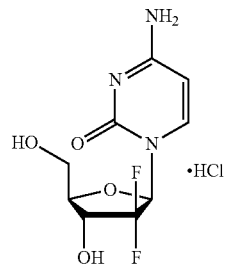

(61) General name: actinomycin-D, antitumor antibiotic formula 25

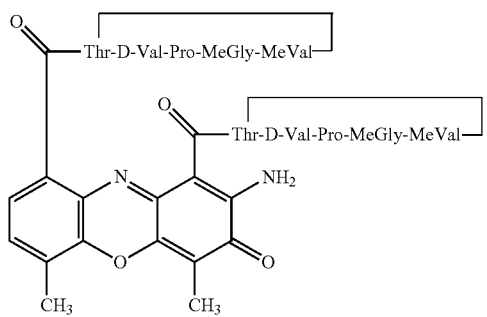

MeGly = N-methylglycine
MeVal = N-methylvaline

(62) General name: aclarubicin hydrochloride, antitumor antibiotic formula 26

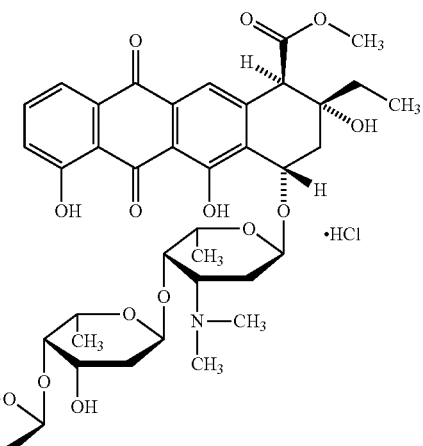

(63) General name: idarubicin hydrochloride, antitumor antibiotic formula 27

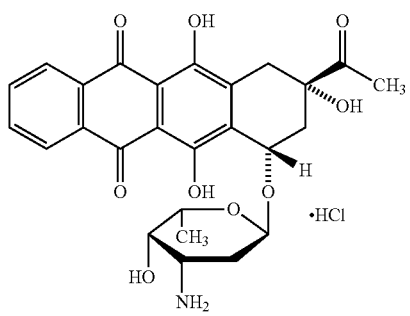

(64) General name: epirubicin hydrochloride, antitumor antibiotic formula 28

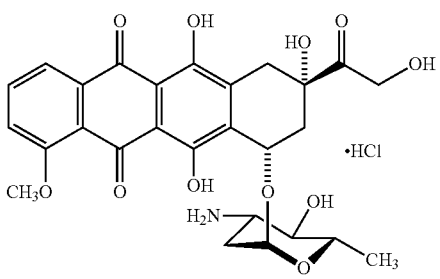

(65) General name: zinostatin stimalamer, antitumor antibiotic formula 29

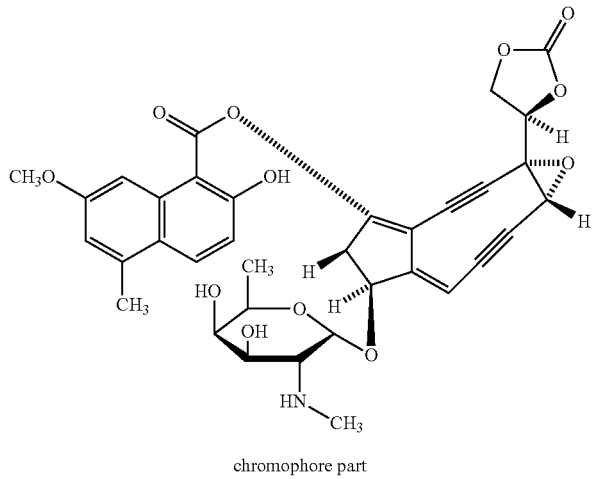

chromophore part

R-Ala-Ala-Pro-Thr-Ala-Thr-Val-Thr-Pro-Ser-Ser-
  R'
  |
Gly-Leu-Ser-Asp-Gly-Thr-Val-Val-Lys-Val-Ala-Gly-
Ala-Gly-Leu-Gln-Ala-Gly-Thr-Ala-Tyr-Asp-Val-Gly-
Gln-Cys-Ala-Trp-Val-Asp-Thr-Gly-Val-Leu-Ala-Cys-
Asn-Pro-Ala-Asp-Phe-Ser-Ser-Val-Thr-Ala-Asp-Ala-
Asp-Gly-Ser-Ala-Ser-Thr-Ser-Leu-Thr-Val-Arg-Arg-
Ser-Phe-Glu-Gly-Phe-Leu-Phe-Asp-Gly-Thr-Arg-
Trp-Gly-Thr-Val-Asp-Cys-Thr-Thr-Ala-Ala-Cys-Gln-
Val-Gly-Leu-Ser-Asp-Ala-Ala-Gly-Asn-Gly-Pro-Glu-
Gly-Val-Ala-Ile-Ser-Phe-Asn apoprotein part $R^1$ and $R^2$ differ from one another and represent the following formulas, respectively, and the same applies to $R'^1$ and $R'^2$.

-continued
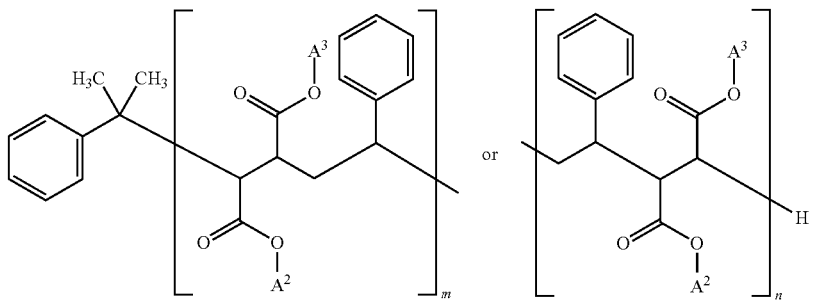
$A^1$ = H or $NH_4$ $A^2$, $A^3$ = H or $NH_4$ or $C_4H_9$ ($A^2$ and $A^3$ do not represent $C_4H_9$ at the same time) M + n: approximately 5.5 on average
(66) General name: daunorubicin hydrochloride, antitumor antibiotic
(67) General name: doxorubicin hydrochloride, antitumor antibiotic
formula30
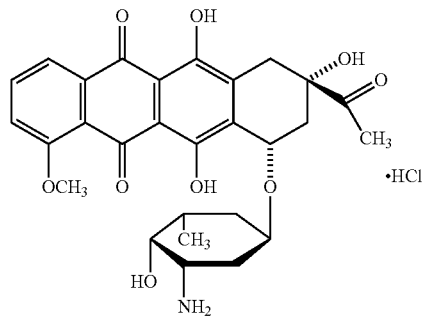
formula31
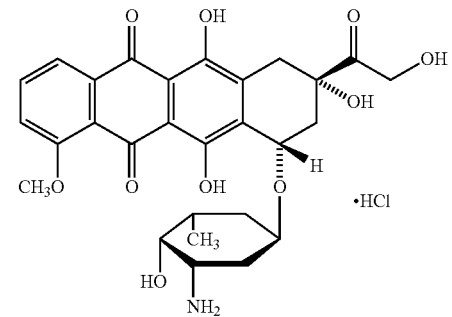
(68) General name: bleomycin hydrochloride, antitumor antibiotic
formula32
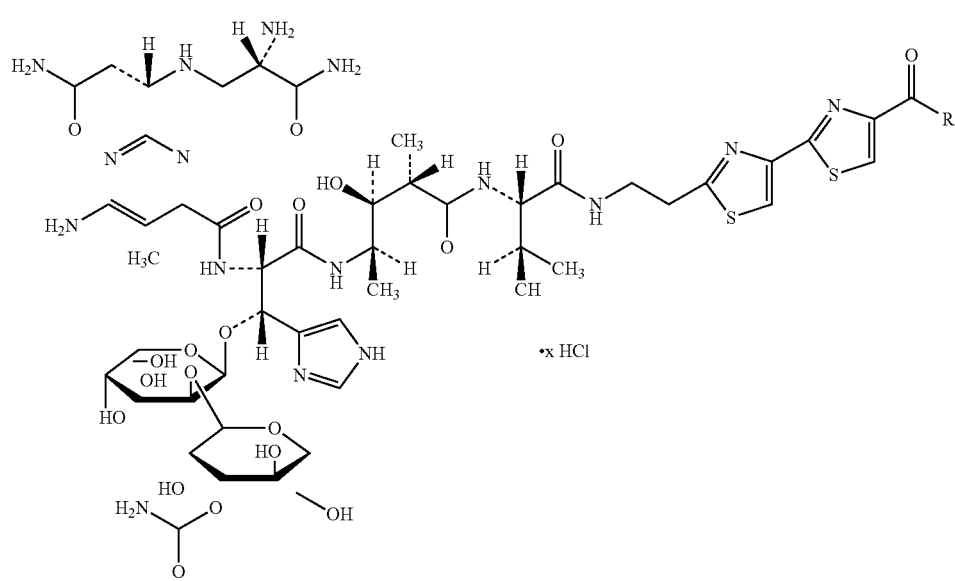

Bleomycin Acid: R = —OH

Bleomycindemethyl-A₂: R = —N(H)—CH₂CH₂CH₂—S—CH₃

Bleomycin A₂₋ₐ: R = —N(H)—(CH₂)₄—NH₂

Bleomycin A₅: R = —N(H)—(CH₂)₃—N(H)—(CH₂)₄—NH₂

Bleomycin B₂: R = —N(H)—(CH₂)₄—N(H)—C(=NH)—NH₂

Bleomycin B₄: R = —N(H)—(CH₂)₄—N(H)—C(=NH)—N(H)—(CH₂)₄—N(H)—C(=NH)—NH₂

Bleomycin A₁: R = —N(H)—CH₂CH₂CH₂—S(=O)—CH₃

Bleomycin A₂: R = —N(H)—CH₂CH₂CH₂—S⁺(CH₃)₂ · X⁻

Bleomycin A₂₋b: R = —N(H)—(CH₂)₃—NH₂

Bleomycin B₁: R = —NH₂

(69) General name: peplomycin sulfate, antitumor antibiotic

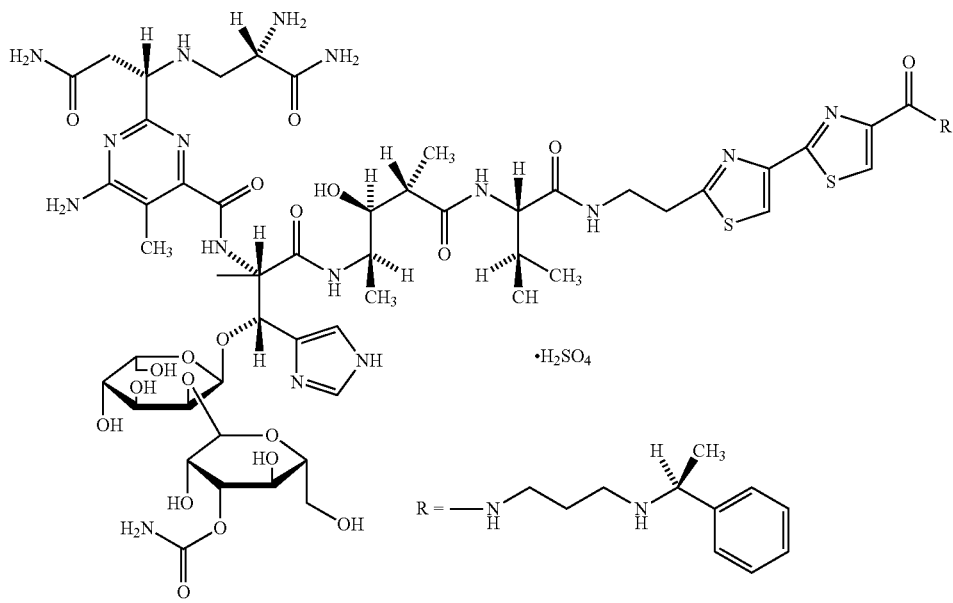

formula33

·H₂SO₄

(70) General name: mitomycin C, antitumor antibiotic

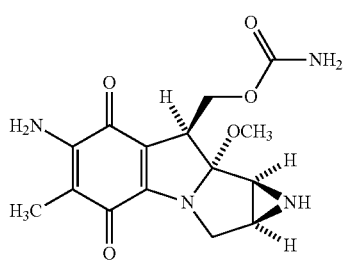

formula34

(71) General name: amrubicin hydrochloride, antitumor antibiotic

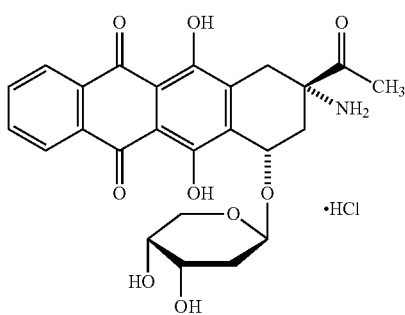

formula35

·HCl

-continued

(72) General name: vibramycin hydrochloride, antitumor antibiotic formula36

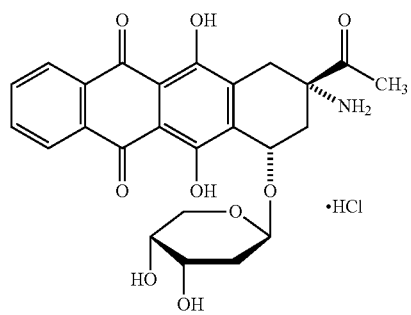

·HCl

(73) General name: pirarubicin hydrochloride, antitumor antibiotic formula37

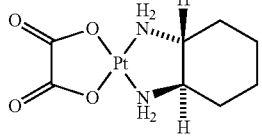

(74) General name: docetaxel hydrate, microtubule inhibitor formula38

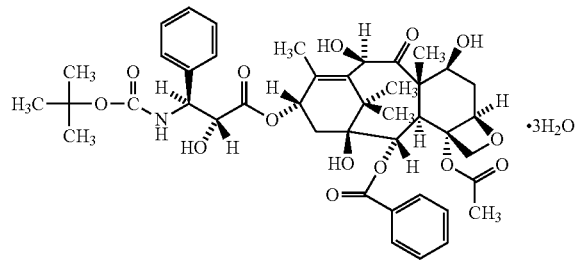

·3H$_2$O

(75) General name: vincristine sulfate, microtubule inhibitor formula39

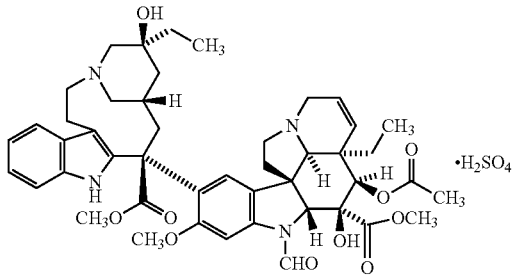

·H$_2$SO$_4$

(76) General name: vinblastine sulfate, microtubule inhibitor formula40

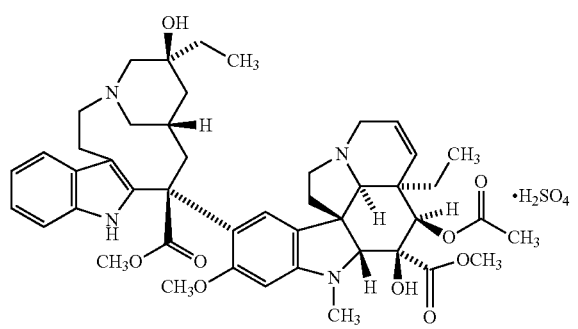

·H$_2$SO$_4$

(77) General name: vinorelbine tartrate, microtubule inhibitor formula41

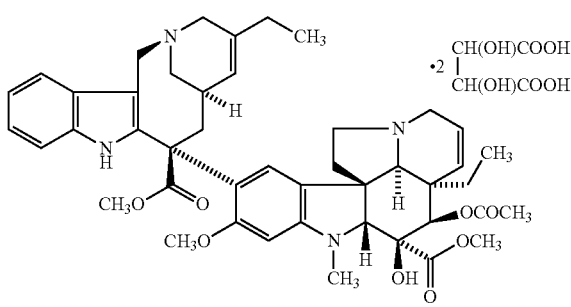

$\cdot 2 \begin{array}{l} CH(OH)COOH \\ | \\ CH(OH)COOH \end{array}$

(78) General name: vindesine sulfate, microtubule inhibitor formula42

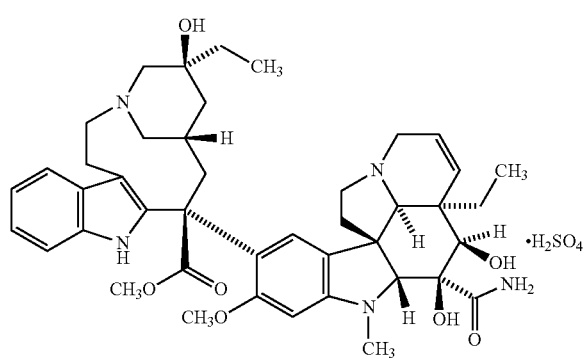

·H$_2$SO$_4$

(79) General name: oxaliplatin, platinum preparation formula43

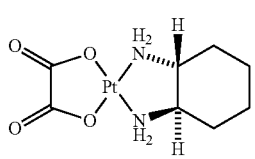

-continued

(80) General name: carboplatin, platinum preparation formula44

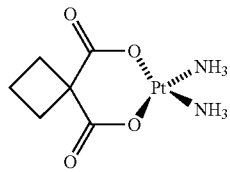

(82) General name: nedaplatin, platinum preparation formula46

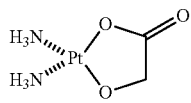

(84) General name: Afema, parahormone drug formula48

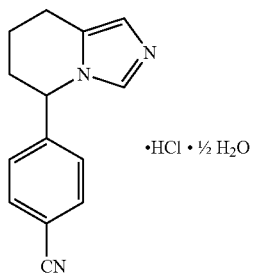

•HCl • ½ H₂O

(86) General name: tamoxifen citrate, parahormone drug formula50

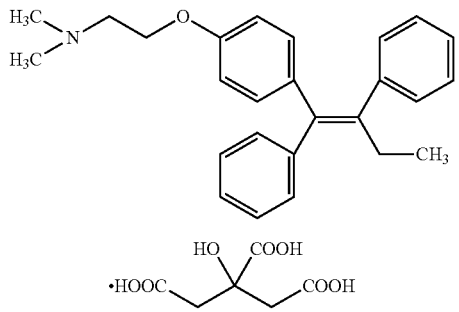

(88) General name: bicalutamide, parahormone drug

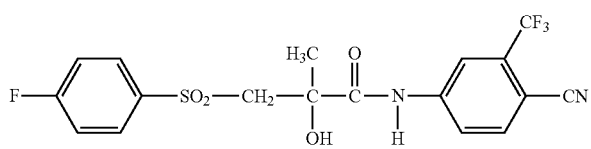

(81) General name: cisplatin, platinum preparation formula45

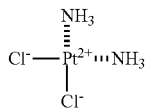

(83) General name: anastrozole, parahormone drug formula47

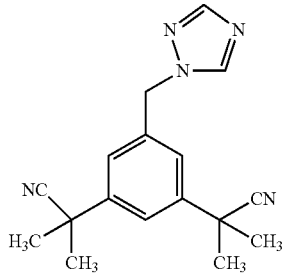

(85) General name: exemestane, parahormone drug formula49

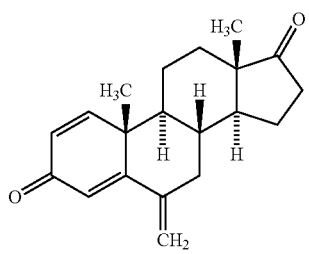

(87) General name: toremifene citrate, parahormone drug formula51

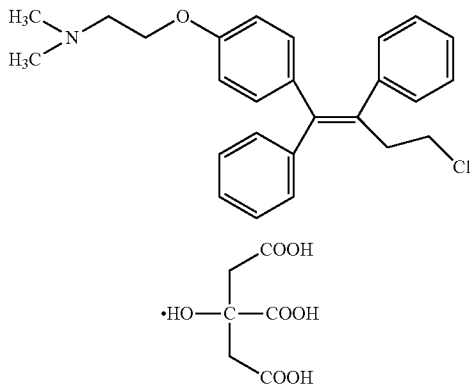

(89) General name: flutamide, parahormone drug formula52 formula53

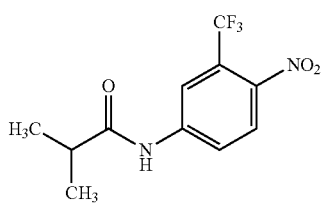

(90) General name: mepitiostane, parahormone drug

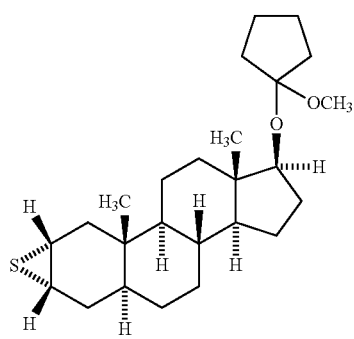

formula54

(91) General name: estramustine sodium phosphate, parahormone drug

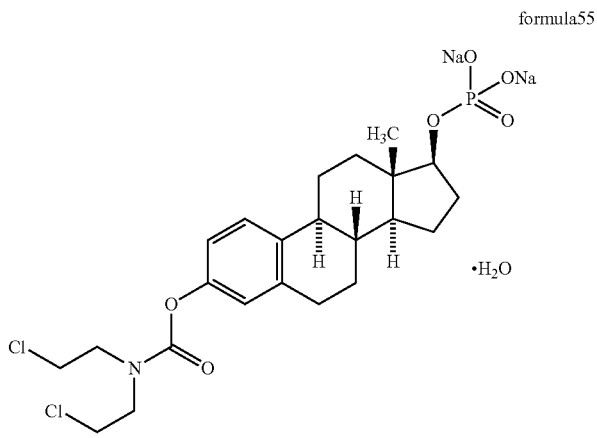

formula55

(92) General name: medroxyprogesterone acetate, parahormone drug

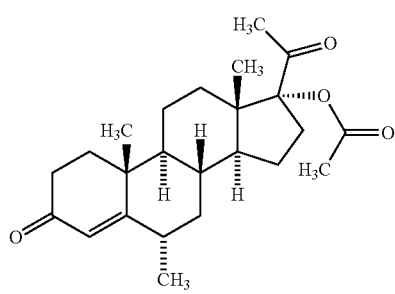

formula56

(93) General name: tamibarotene, molecular target therapeutic drug

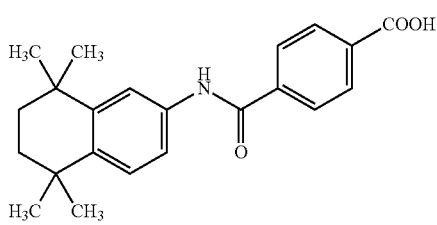

formula57

(94) General name: Gefitinib, molecular target therapeutic drug

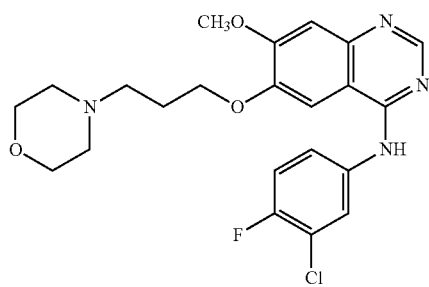

formula58

(95) General name: tretinoin, molecular target therapeutic drug

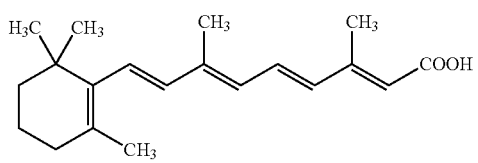

formula59

(96) General name: imatinib mesylate, molecular target therapeutic drug

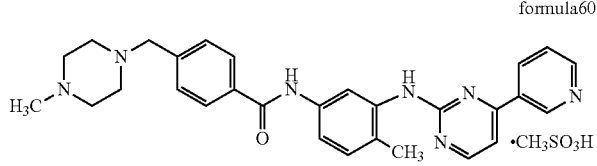

formula60

(97) General name: etoposide, topoisomerase inhibitor

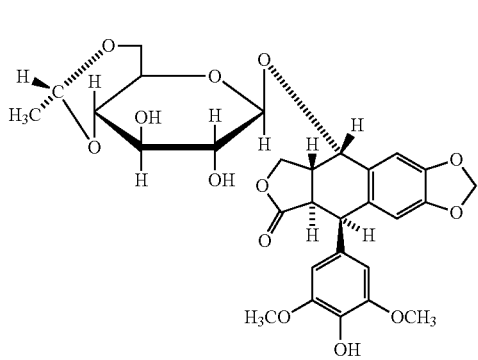

formula61

(98) General name: sobuzoxane, topoisomerase inhibitor formula62

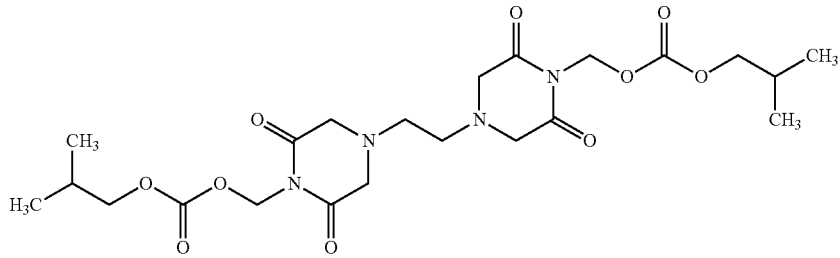

(99) General name: irinotecan hydrochloride, topoisomerase inhibitor formula63

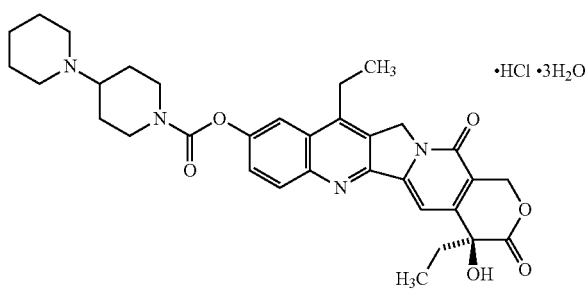

(100) General name: nogitecan hydrochloride, topoisomerase inhibitor formula64

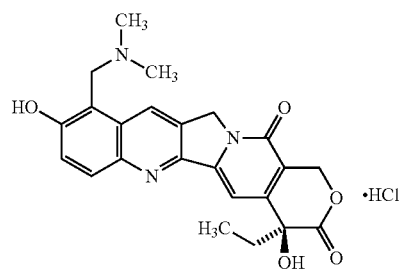

(101) General name: ubenimex, nonspecific immunopotentiator formula65

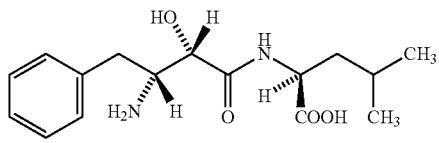

(102) General name: sizofiran, nonspecific immunopotentiator formula66

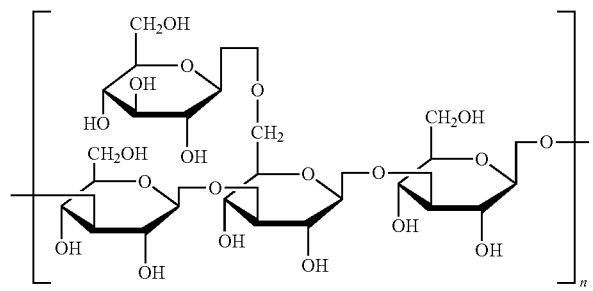

(103) General name: lenthinan, nonspecific immunopotentiator formula67

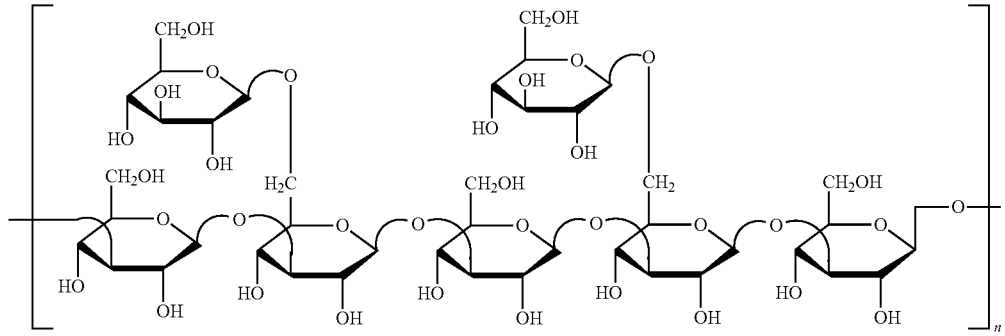

Furthermore, the present invention provides an antineoplastic drug having a self-magnetic metal-salen complex compound wherein $R_3$ is composed of any one of compounds represented by the following formulas (104) to (109).

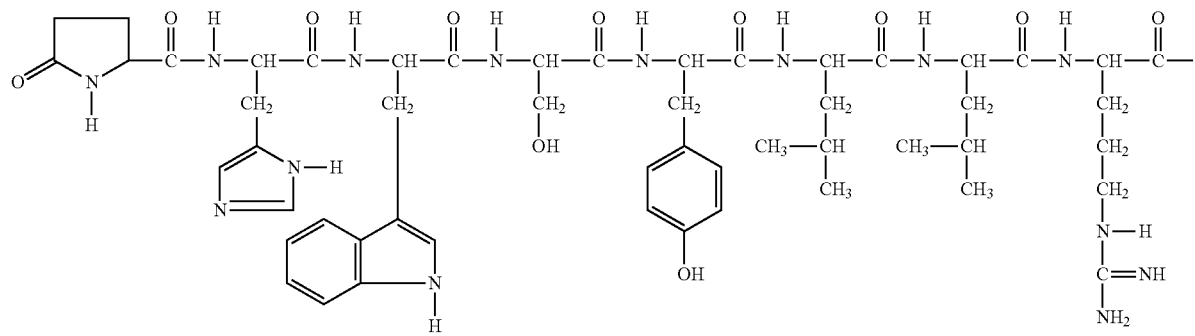
Product name: Leuplin; and general name: leuprorelin acetate, anti-tumor agent
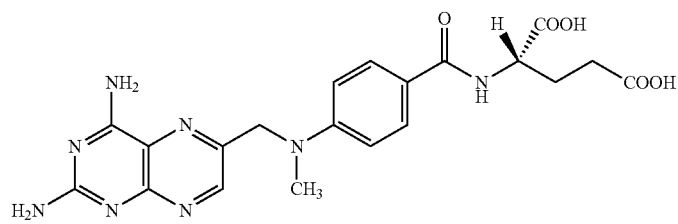
Product name: methotrexate; and general name: methotrexate, anti-tumor agent
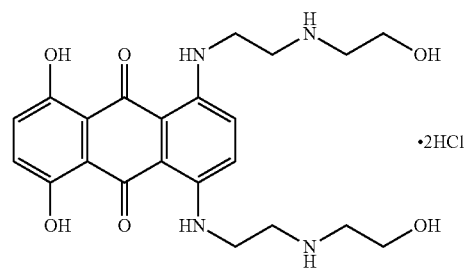
Product name: Novantrone; and general name: mitoxantrone hydrochloride, anti-tumor agent
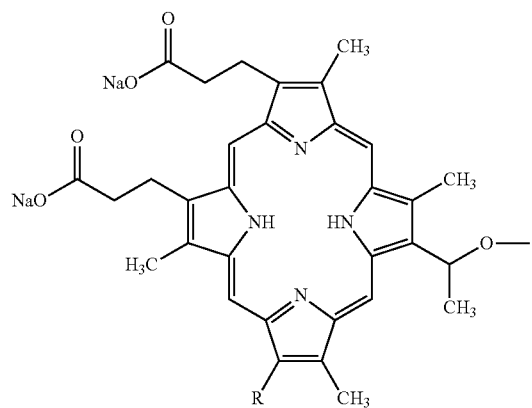
Product name: photofrin; and general name: porfimer sodium, anti-tumor agent

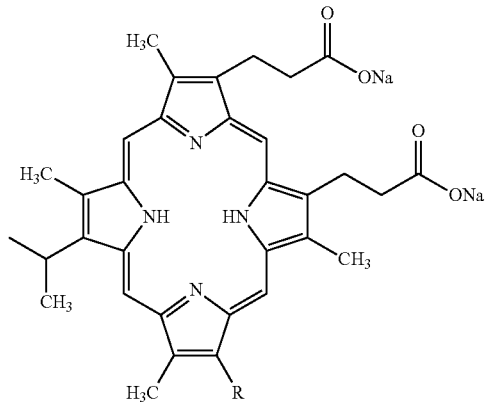

Product name: photofrin; and general name: porfimer sodium, anti-tumor agent

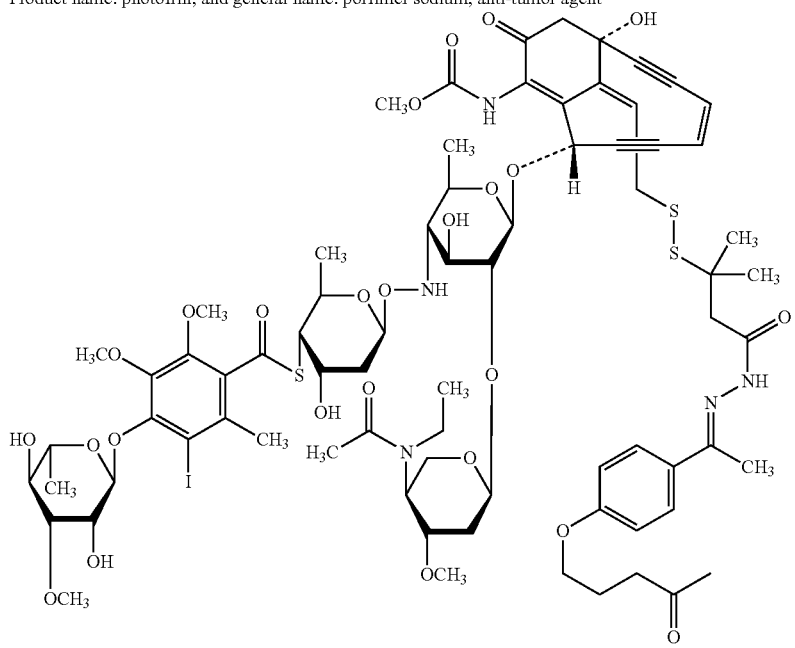

Product name: Mylotarg; and general name: gemtuzumab ozogamicin, anti-tumor agent

Advantageous Effects of Invention

According to the present invention, it is possible to provide a metal-salen complex compound, which exhibits excellent noninvasiveness and can be efficiently transferred to an affected site, a local anesthetic containing this metal-salen complex compound, and an antineoplastic drug containing this metal-salen complex compound.

DESCRIPTION OF EMBODIMENTS

Example 1

Figure 1:
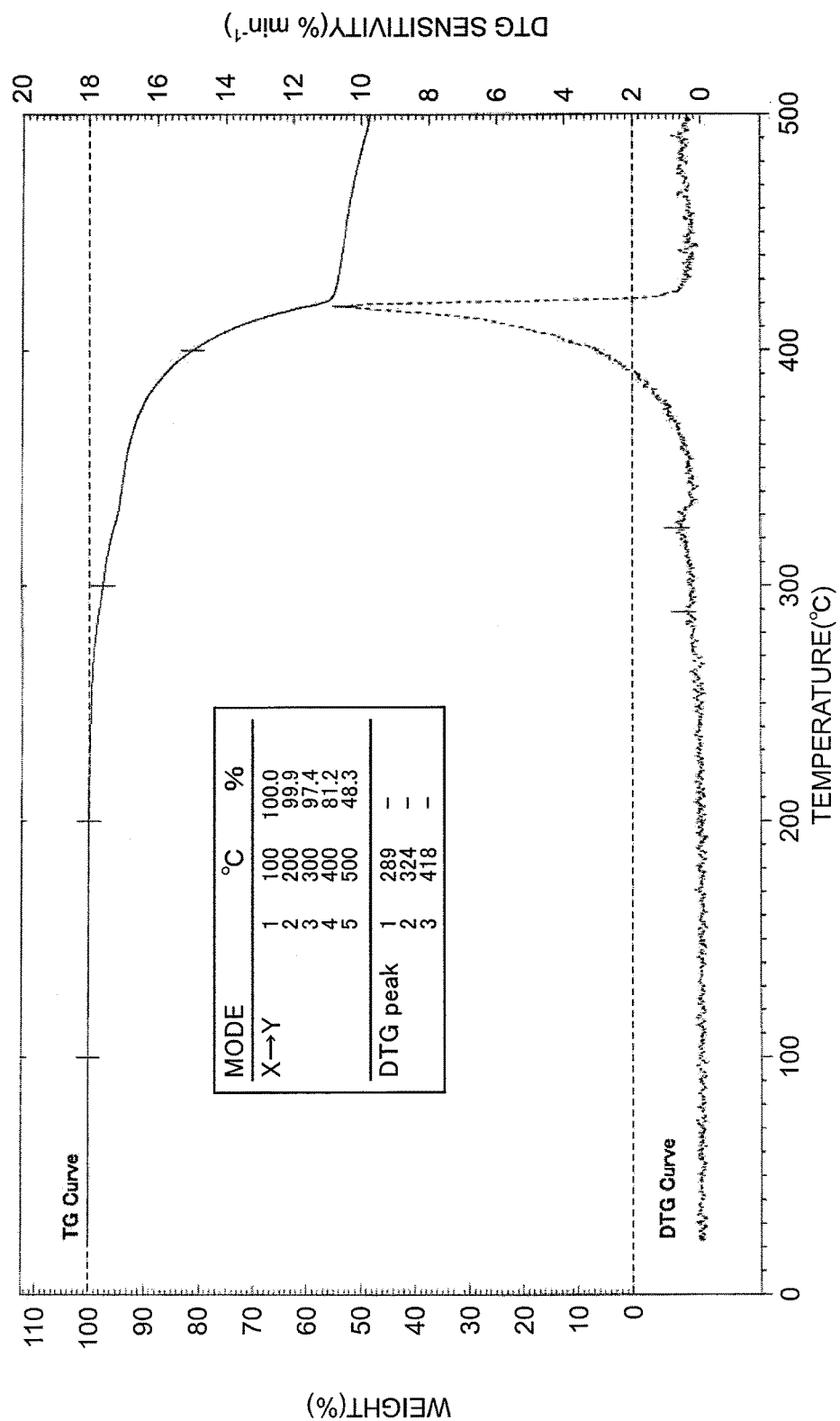
FIG. 1 is a graph showing changes in weight (TG) and the results of differential thermal analysis (DTA) with respect to metal-salen complex compounds according to the present invention.

A metal-salen complex compound according to the present invention was produced in the following manner.

Step 1

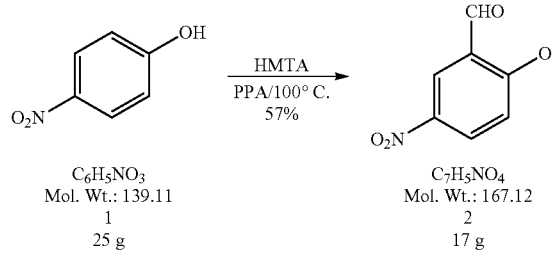

A mixture of 4-nitrophenol (Compound 1) (25 g, 0.18 mol), hexamethylene tetramine (25 g, 0.18 mol), and polyphosphoric acid (200 ml) were stirred for one hour at the temperature of 100 degrees Celsius. Then, that mixture was introduced to 500 ml of ethyl acetate and 1 L (liter) of water and stirred until it completely dissolved. Furthermore, when 400 ml of ethyl acetate was added to that solution, the solution separated into two phases. Subsequently, the aqueous phase was removed from the solution which separated into the two phases; and the remaining compound was washed twice with a basic solvent and dried over anhydrous $MgSO_4$ (magnesium sulfate). As a result, 17 g of Compound 2 (57% yield) was synthesized.

Step 2

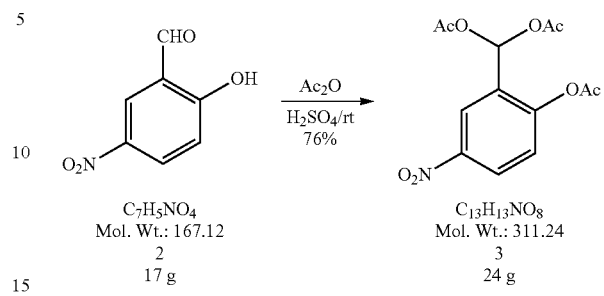

Compound 2 (17 g, 0.10 mol), acetic anhydride (200 ml) and $H_2SO_4$ (minimal) were stirred for one hour at room temperature. The resulting solution was mixed for 0.5 hour in iced water (2 L) to bring about hydrolysis. The resulting solution was filtered and dried in air, thereby obtaining white powder. The powder was recrystallized, using a solvent containing ethyl acetate. As a result, 24 g of Compound 3 (76% yield) was obtained in the form of white crystals.

Step 3

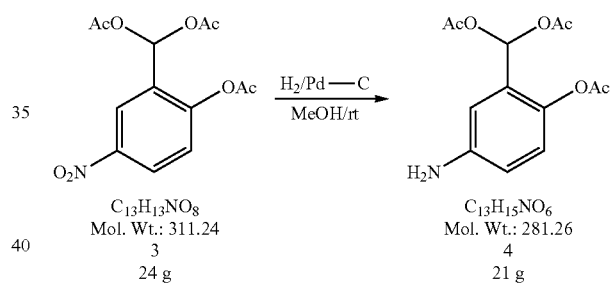

A mixture of carbon (2.4 g) supporting 10% palladium with Compound 3 (24 g, 77 mmol) and methanol (500 ml) was reduced over night in a 1.5 atm hydrogen reducing atmosphere. After the reduction was completed, the product was filtered, thereby allowing 21 g of Compound 4 in the form of brown oil to be synthesized.

Step 4, 5

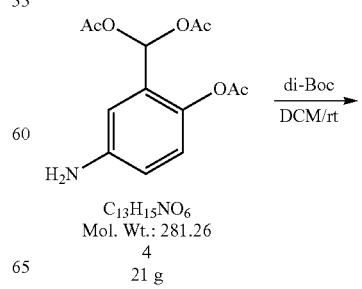

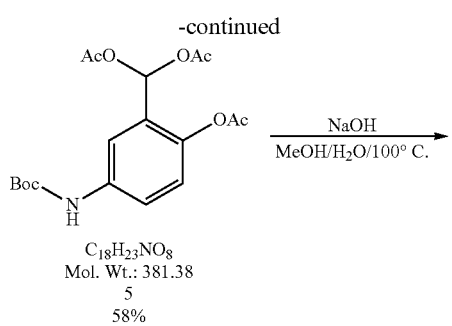

C₁₈H₂₃NO₈
Mol. Wt.: 381.38
5
58%

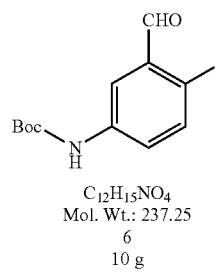

C₁₂H₁₅NO₄
Mol. Wt.: 237.25
6
10 g

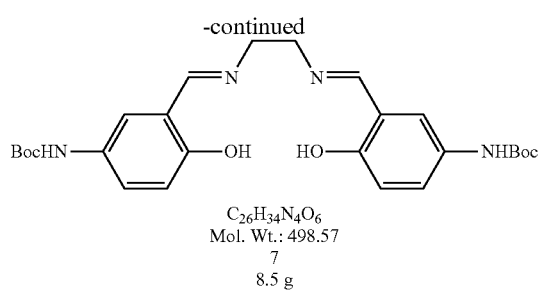

C₂₆H₃₄N₄O₆
Mol. Wt.: 498.57
7
8.5 g

Compound 6 (10 g, 42 mmol) was introduced into 400 ml of anhydrous ethanol, the mixture was brought to reflux while heated, and several drops of ethylene diamine (1.3 g, 21 mmol) were added into 20 ml of anhydrous ethanol while stirred for 0.5 hour. The mixture was introduced into a container of ice, where it was cooled and mixed for 15 minutes. It was then washed with 200 ml of ethanol, filtered, and dried in a vacuum, thereby obtaining 8.5 g (82% yield) of Compound 7.

Step 7

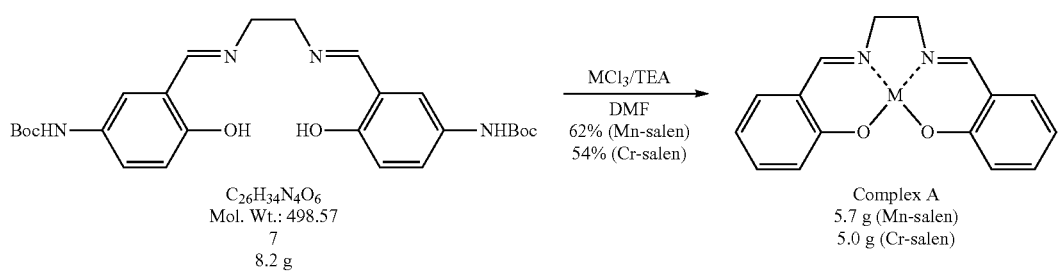

C₂₆H₃₄N₄O₆
Mol. Wt.: 498.57
7
8.2 g

Complex A
5.7 g (Mn-salen)
5.0 g (Cr-salen)

Compound 4 (21 g, 75 mmol) and di(tert-butyl) dicarbonate (18 g, 82 mmol) were stirred over night in anhydrous dichloromethane (DCM) (200 ml) in a nitrogen atmosphere. The resulting solution (Compound 5) was allowed to evaporate in a vacuum and then dissolved in methanol (100 ml). Sodium hydroxide (15 g, 374 mmol) and water (50 ml) were then added and the solution was brought to reflux for 5 hours. The solution was then cooled, filtered, washed with water, and allowed to dry in a vacuum, thereby obtaining a brown compound. The resulting compound was processed twice by flash chromatography using silica gel, thereby obtaining 10 g of Compound 6 (58% yield).

Step 6

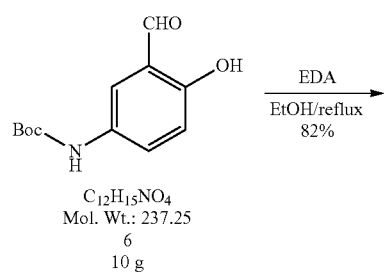

C₁₂H₁₅NO₄
Mol. Wt.: 237.25
6
10 g

Compound 7 (8.2 g, 16 mmol) and triethylamine (22 ml, 160 mmol) were introduced into normal methanol (methanol made by Showa Chemical, purity 99.5% or more) (50 ml); and a solution of FeCl₃·4H₂O (iron (III) chloride tetrahydrate) (2.7 g, 16 mmol) in a case of a Fe salen complex compound, MnCl₃·4H₂O (manganese (III) chloride tetrahydrate) (2.7 g, 16 mmol) in a case of a Mn salen complex compound, or CrCl₃·4H₂O (chromium (III) chloride tetrahydrate) (2.7 g, 16 mmol) in a case of a Cr salen complex compound added to 10 ml of methanol was mixed in a nitrogen atmosphere. Moreover, it is possible to use CoCl₂ (cobalt (II) chloride produced by Alfa Aesar) in a case of a Co salen complex compound, NiCl₂ (nickel (II) chloride produced by Alfa Aesar) in a case of a Ni salen complex compound, MoCl₃ (molybdenum (III) chloride produced by Alfa Aesar) in a case of a Mo salen complex compound, RuCl₃ (ruthenium (III) chloride produced by Alfa Aesar) in a case of a Ru salen complex compound, RhCl₃ (rhodium (III) chloride produced by Alfa Aesar) in a case of a Rh salen complex compound, PdCl₂ (palladium (II) chloride produced by Alfa Aesar) in a case of a Pd salen complex compound, WCl₆ (tungsten(VI) chloride produced by Alfa Aesar) in a case of a W salen complex compound, ReCl₅ (rhenium (V) chloride produced by Alfa Aesar) in a case of a Re salen complex compound, osmium salen trihydrate (osmium (III) chloride trihydrate produced by Alfa Aesar) in a case of an Os salen complex compound, IrCl₃ (iridium (III) chloride produced by Alfa Aesar) in a case of an Ir salen complex compound, $PtCl_2$ (platinum (II) chloride produced by Alfa Aesar) in a case of a Pt salen complex compound, $NdCl_3$ (neodymium (III) chloride produced by Alfa Aesar) in a case of a Nd salen complex compound, $SmCl_3$ (samarium (III) chloride produced by Alfa Aesar) in a case of a Sm salen complex compound, $EuCl_3$ (europium (III) chloride produced by Alfa Aesar) in a case of a Eu salen complex compound, and $GdCl_3$ (gadolinium (III) chloride produced by Alfa Aesar) in a case of a Gd salen complex compound.

The ingredients were mixed for one hour in a nitrogen atmosphere at the room temperature, thereby obtaining a brown compound. Subsequently, this compound was then dried in a vacuum or its water was dried sufficiently by, for example, using magnesium, or was adsorbed and removed by magnesium. The resulting compound was diluted with 400 ml of dichloromethane, washed twice with a basic solution, dried in $Na_2SO_4$, and dried in a vacuum, thereby obtaining a metal-salen complex compound of a dimer containing water molecules. The resulting compound was recrystallized in a solution of diethyl ether and paraffin, and assay by high-speed liquid chromatography revealed a dimeric metal-salen complex compound containing water molecules of purity of 95% or higher.

The chemical structure formulas of the obtained dimer with water molecules are as follows.

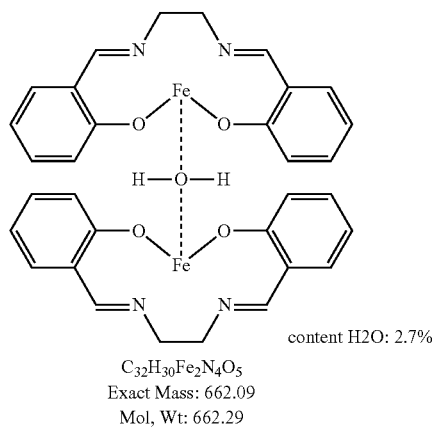

Formula (IV)

content H2O: 2.7%

$C_{32}H_{30}Fe_2N_4O_5$
Exact Mass: 662.09
Mol, Wt: 662.29
m/e: 662.09 (100.0%), 663.09 (41.6%), 660.09 (12.9%), 664.10 (9.0%), 661.10 (4.7%), 665.10 (1.5%), 664.09 (1.3%), 662.10 (1.1%)
C, 58.03; H, 4.57; Fe, 16.86; N, 8.46; O, 12.08

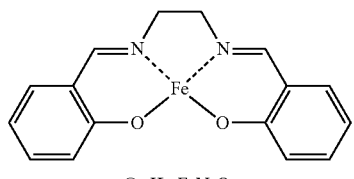

Formula (V)

$C_{16}H_{14}FeN_2O_2$
Exact Mass: 322.04
Mol, Wt: 322.14
m/e: 322.04 (100.0%), 323.04 (20.4%), 320.05 (6.4%), 324.05 (1.5%), 324.04 (1.3%), 321.05 (1.1%)
C, 59.65; H, 4.38; Fe, 17.34; N, 8.70; O, 9.93

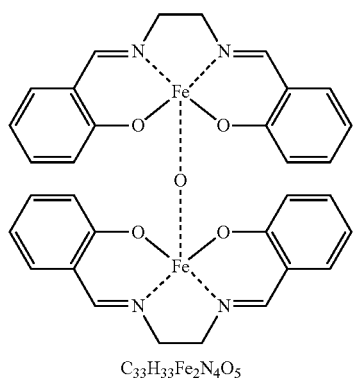

Formula (VI)

$C_{33}H_{33}Fe_2N_4O_5$
Exact Mass: 675.1
Mol, Wt: 675.31
m/e: 675.10 (100.0%), 676.10 (41.9%), 673.10 (12.7%), 677.11 (6.4%), 674.11 (4.6%), 677.10 (4.0%), 678.11 (1.4%), 675.11 (1.0%)
C, 58.69; H, 4.63; Fe, 16.54; N, 8.30; O, 11.85

Incidentally, the bond between the metal and oxygen can be considered as a fusion of a covalent bond and a metallic bond. Elemental analysis of the obtained dimer with water molecules revealed that it contained 57.73% C, 4.42% H, 17.2% Fe, 8.49% N, and 12.16% O; and all differences between calculated values and experimental values were within an absolute error range of ±0.4%.

Moreover, when the Mn salen complex compound or the Cr salen complex compound is used in the above examples, each Fe in the above chemical formulas becomes Mn or Cr.

Figure 2:
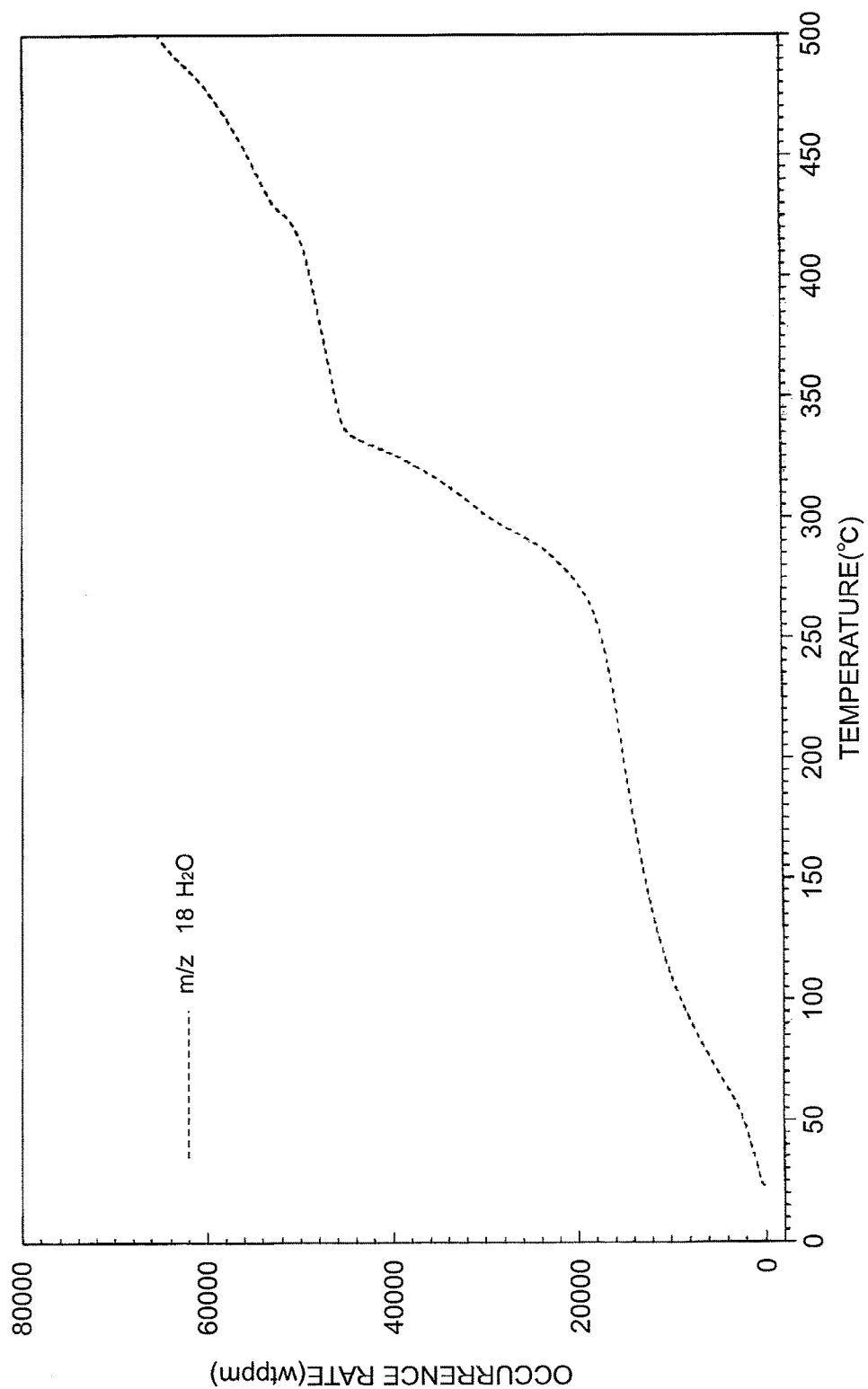
FIG. 2 is a diagram showing an integral curve of the metal-salen complex compounds according to the present invention.

Next, TG-Mass analysis was performed in order to clarify the existence of the included water molecules. As a result, it was found that water molecules were detected within the range from room temperature to 260 degrees Celsius. This is because the water molecules are incorporated into crystals. The results of the TG-Mass analysis are shown in FIG. 1 and FIG. 2.

Incidentally, experimental conditions for the TG-Mass analysis are described below.
TG Device: TG-40 by SHIMADZU CORPORATION
MS Device: GC/MS QP2010(1) by SHIMADZU CORPORATION
Measurement Conditions
Before starting measurement: after setting the sample on the TG device, feed carrier gas for 15 minutes or more and then start increasing the temperature
Heating condition: from room temperature to 500 degrees Celsius (temperature rise speed: 5 degrees Celsius/min)
Sample Weight: 3.703 mg
MS Sensitivity: 1.80 kV
Mass Number Range: m/z=10-300
Atmosphere: helium (50 ml/min)
Standard Reference Material: sodium tungstate dihydrate, 1-butene, carbon dioxide Example 2

Figure 3:
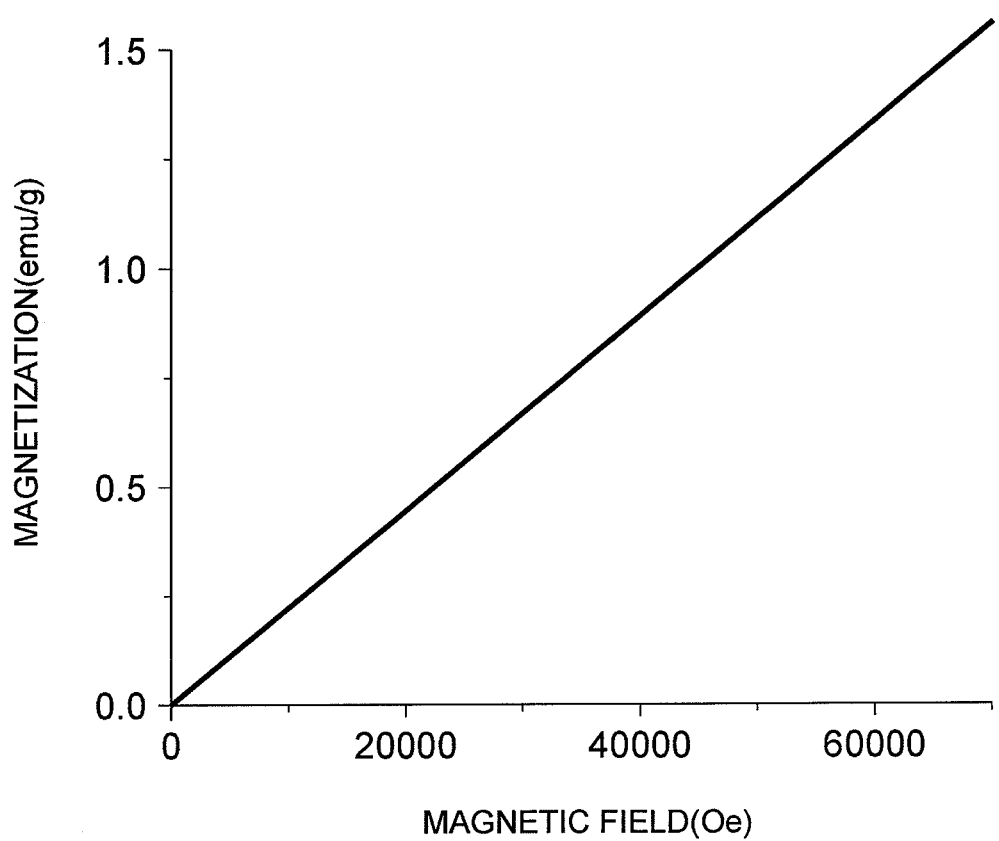
FIG. 3 is a diagram showing a magnetic field-magnetization curve of a Mn salen complex compound.

A magnetic field-magnetization curve of the Mn salen complex compound obtained by the above-described method at 37 degrees Celsius (310 K) was measured by using MPMS7 by Quantum Design, Inc. and the measurement revealed that the Mn salen complex compound was paramagnetic. FIG. 3 shows the results.

Example 3

Figure 4:
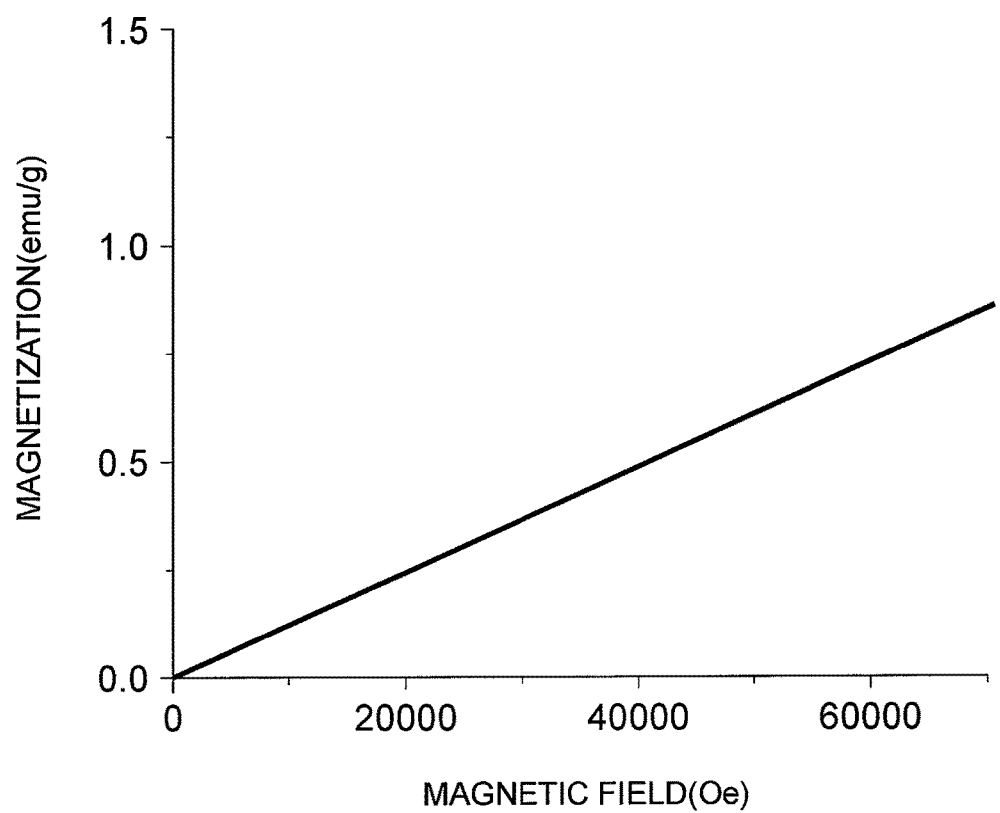
FIG. 4 is a diagram showing a magnetic field-magnetization curve of a Cr salen complex compound.

A magnetic field-magnetization curve of the Cr salen complex compound obtained by the above-described method at 37 degrees Celsius (310 K) was measured by using MPMS7 by Quantum Design, Inc. and the measurement revealed that the Cr salen complex compound was paramagnetic. FIG. 4 shows the results.

Example 4

Figure 6:
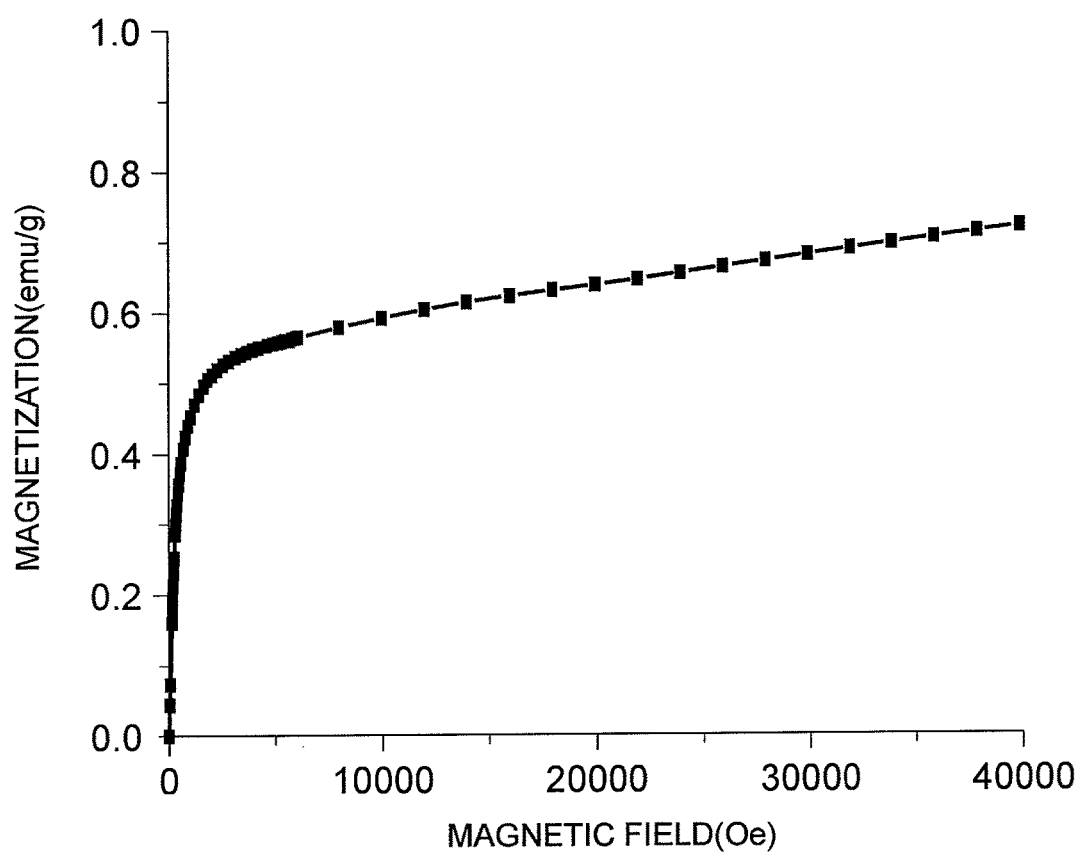
FIG. 6 shows a magnetic field-magnetization curve of a Fe salen complex compound.

A magnetic field-magnetization curve of the Co salen complex compound obtained by the above-described method at 37 degrees Celsius (310 K) was measured by using MPMS7 by Quantum Design, Inc. and the measurement revealed that the Co salen complex compound was paramagnetic. FIG. 6 shows the results.

Example 5

Figure 5:
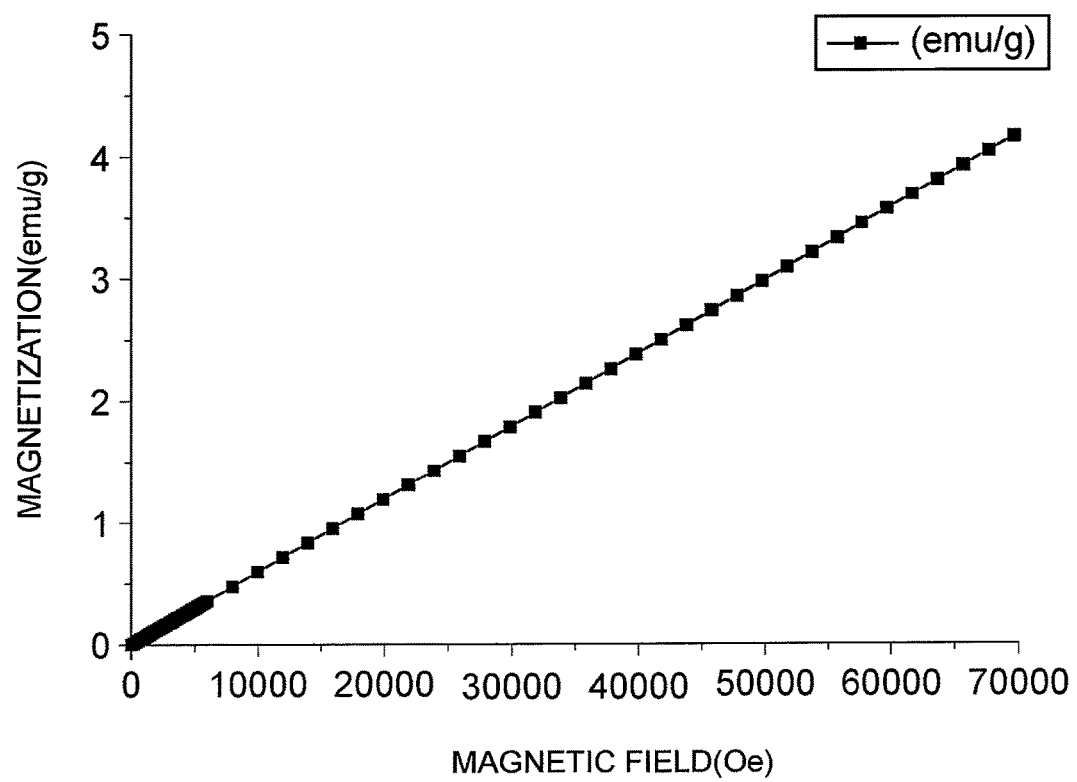
FIG. 5 is a diagram showing a magnetic field-magnetization curve of a Co salen complex compound at 37° C. (310 K).

FIG. 6 shows a magnetic field-magnetization curve of the Fe salen complex compound at 37 degrees Celsius (310 K). FIG. 3, FIG. 5, and FIG. 6 show that as compared with the Fe salen complex compound, the Co salen complex compound has larger magnetization when the magnetic field is 10000 Oe (oersted; (1 T (tesla))) or more. Moreover, as compared with the Fe salen complex compound, the Mn salen complex compound has larger magnetization when the magnetic field is 30000 Oe (3 T) or more. Therefore, the Fe salen complex compound has the largest magnetization when the magnetic field is less than 10000 Oe (1 T); and is suited for use in magnetic induction drug delivery systems which use, for example, neodymium permanent magnets. However, when the magnetic field exceeds 10000 Oe (1 T), the Co salen complex compound or the Mn salen complex compound has large magnetization and is most suited for magnetic induction drug delivery systems which use superconducting magnets.

Example 6

Figure 7:
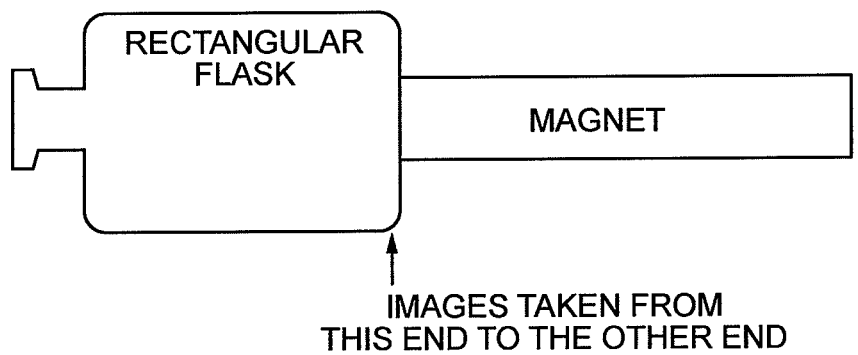
FIG. 7 is a diagrammatic illustration of a state where a bar magnet is made to be in contact with a rectangular flask.

Culture medium was sprinkled with metal-salen complex compound powder, which is obtained with respect to each of the Fe salen complex compound, the Mn salen complex compound, the Cr salen complex compound, and the Co salen complex compound by the above-described method, in amounts allowing magnetic attraction to be visibly observed at a rat L6 cell confluence of 30%, and the state of the medium was photographed after 48 hours. Incidentally, FIG. 7 shows a bar magnet in contact with a rectangular flask containing rat L6 cell culture medium.

Figure 8:
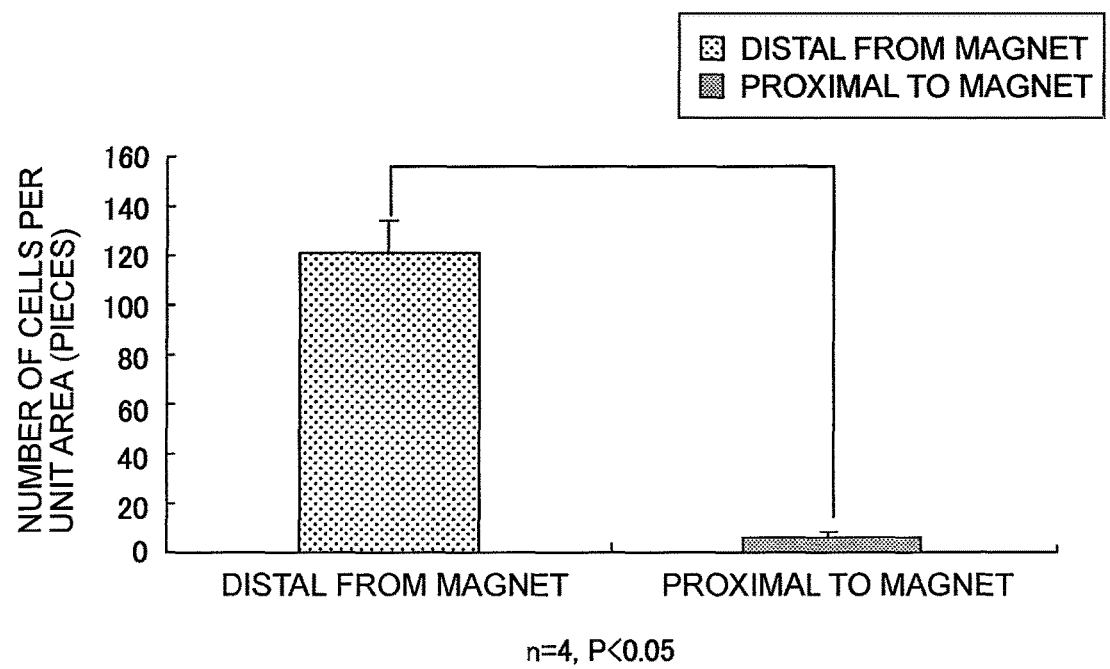
FIG. 8 is a characteristic diagram showing the relationship between the distance from the magnet and the number of cells (pieces) per unit area.

Then, after 48 hours, the bottom face of the rectangular flask was photographed from one end to the other, and the cell count was calculated. Of the results of such calculation, the results of the Fe salen complex compound are shown in FIG. 8. Incidentally, Referring to FIG. 8, a "position proximal to the magnet" means within a projection area of the magnet end surface at the bottom of the rectangular flask, and a "position distal to the magnet" means a region on the side opposite the magnet end surface at the bottom of the rectangular flask.

FIG. 8 shows that, near the magnet, the Mn salen complex was attracted, resulting in a greater Fe-salen complex concentration, so that the DNA-growth inhibition action of the Fe-salen complex resulted in a dramatically lower number of cells than the position distal to the magnet. Moreover, regarding each of the Mn salen complex compound, the Cr salen complex compound, and the Co salen complex compound, the results of a dramatically lower number of cells were obtained at the position proximal to the magnet than the position distal to the magnet. As a result, the magnetic drugs and the system equipped with magnetism-generating means according to the present invention can thus allow the drugs to become concentrated in target tissues and tissues of individuals.

Figure 9:
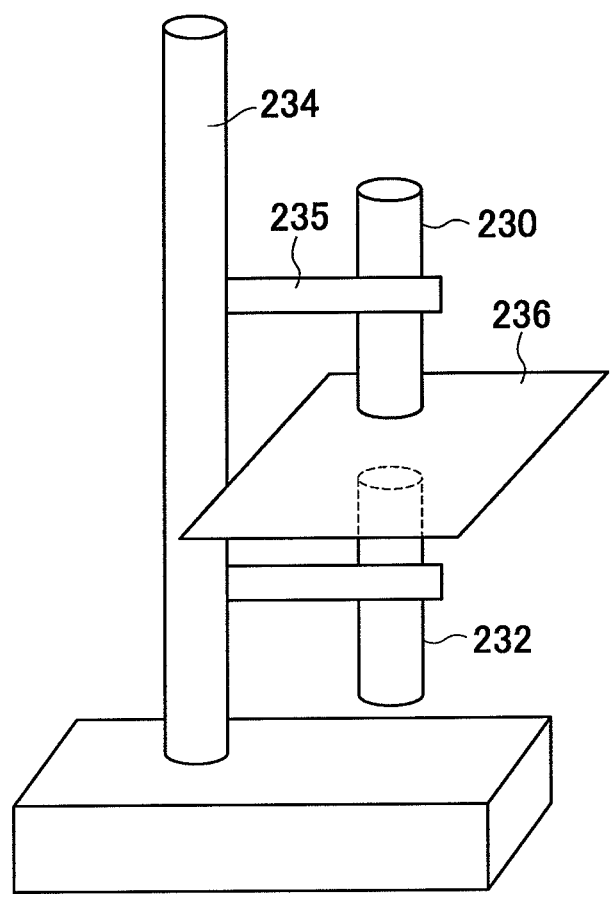
FIG. 9 is a perspective view of a guidance system.

Next, an guidance example using a guidance system will be described. In this guidance system, as illustrated in FIG. 9, a pair of magnets 230 and 232 facing each other in the direction of gravity are supported by a stand 234 and clamp 235, and a metal plate 236 is located between the magnets 230 and 232. The metal plate 236, especially an iron plate, is placed between the pair of magnets 230 and 232 so that a magnetic field of locally uniform and strong strength can be created. An electrical magnet can be used instead of a magnet to modify the magnetic force generated in this guidance system. The magnetism-generating means can be moved to a target position of the individual on a table to allow the pair of magnetism-generating means to move in the X, Y, and Z directions. The tissue of an individual can be placed in the region of the magnetic field to concentrate the drug in the tissue.

More specifically, for example, the aforementioned Fe salen complex compound (drug concentration: 5 mg/mL (15 mM)) was injected intravenously into a mouse weighing about 30 g, a laparotomy was performed, and the mouse was placed on the iron plate 236 to locate its right kidney between the pair of magnets 230 and 232. Incidentally, the magnets used were Product No. N50 (neodymium permanent magnets) by Shin-Etsu Chemical Co., Ltd. with a residual flux density of 1.39 to 1.44 T. Under this circumstance, the magnetic field applied to the right kidney was about 0.3 (T), and the magnetic field applied to its left kidney was about ⅒ of the above-mentioned magnetic field.

Figure 10:
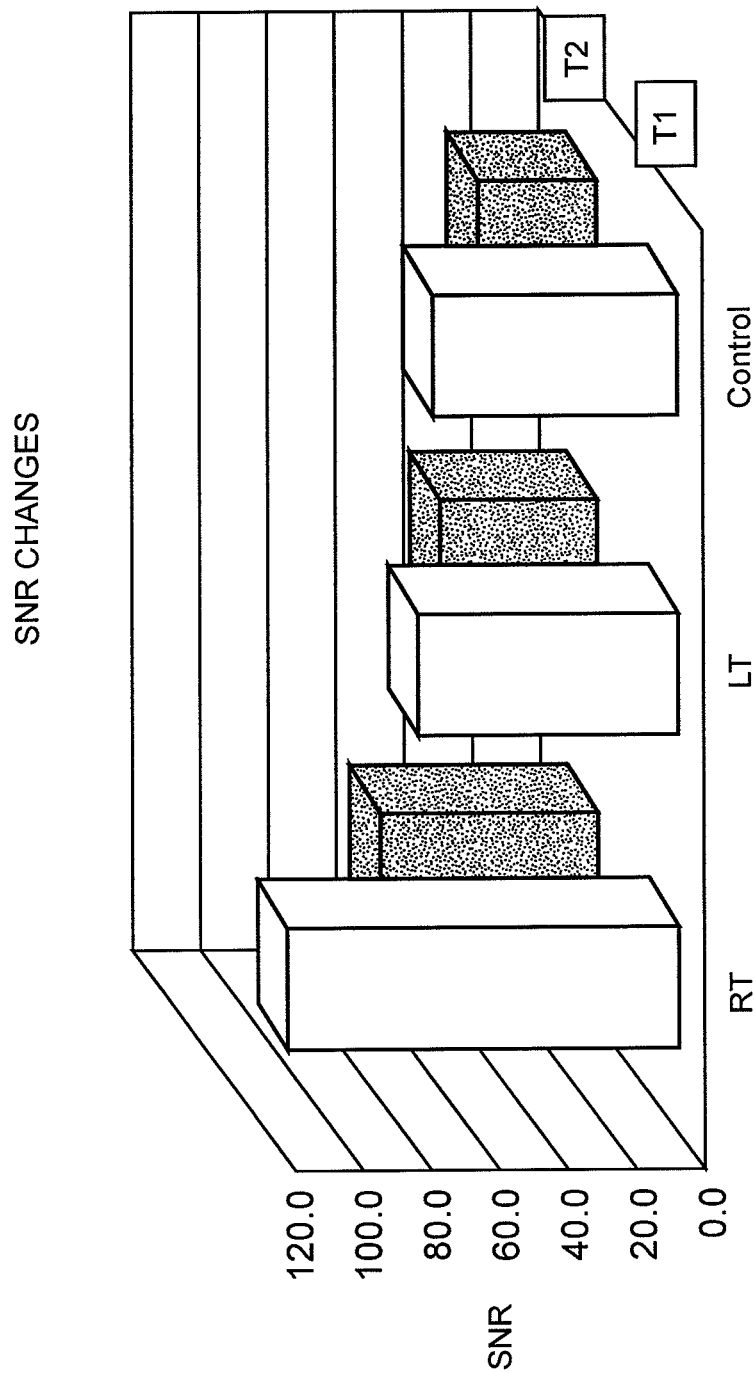
FIG. 10 is a characteristic diagram showing SNR measurement results of cells after being placed on the guidance system by using MRI.

Together with the left kidney and a kidney to which no field was applied (control), a magnetic field was applied to the right kidney of the mouse; and after 10 minutes the SNR was measured by MRI in T1 mode and T2 mode. As shown in FIG. 10, it was confirmed that it was possible to make the drug stay in the right kidney (RT) to which the magnetic field was applied, as compared to the left kidney (LT) and the control.

Furthermore, when each of the Mn salen complex compound, the Cr salen complex compound, and the Co salen complex compound was injected intravenously into a mouse, a laparotomy was performed, and a magnetic field was applied to the mouse by using the guidance system shown in FIG. 9 in the same manner, it was confirmed that it was possible to make the drug stay in the right kidney (RT) to which the magnetic field was applied, as compared to the left kidney (LT) and the control.

Figure 11:
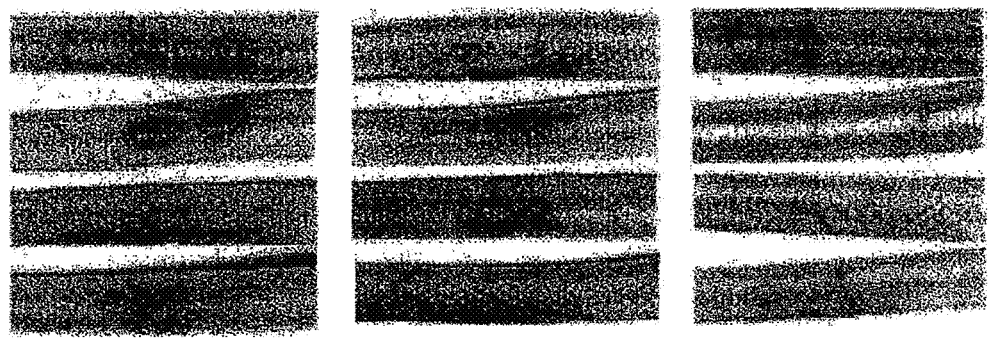
FIGS. 11A-11C are photographs each showing the effects of the Fe salen complex compound on melanoma growth in mice.

FIGS. 11A-11C show the effect of the Fe salen complex compound on melanoma growth in mice. Melanoma was established in mouse tails in vivo by local grafting of cultured melanoma cells (Clone M3 melanoma cells). Incidentally, FIG. 11A is a photograph showing the effects of a saline group (saline) into which the saline water was injected instead of the Fe salen complex compound; FIG. 11B is a photograph showing the effects of a group (SC) into which the Fe salen complex compound was injected without applying the magnetic field; and FIG. 11C is a photograph showing the effect of a group (SC+Mag) into which the Fe salen complex compound was injected while applying the magnetic field (n=7-10).

The Fe salen complex compound (50 mg/kg) was administered intravenously via tail vein, followed by local application of a magnetic field by the use of a commercially available bar magnet (630 mT, a cylindrical neodymium magnet, 150 mm long and 20 mm in diameter). Application of a bar magnet was performed with 3 hour gentle contact with the site of melanoma immediately after injection of the Fe salen complex compound for 10-14 days.

Application of the bar magnet was performed in such a way so that the magnetic field strength became maximal over the area of expected melanoma extension, which was approximately 150 mm or shorter in a mouse tail for a growth period of 2 weeks. Twelve days after the initial injection of the Fe salen complex compound, the extension of melanoma was evaluated by assessing the area of melanoma pigmentation.

Figure 12:
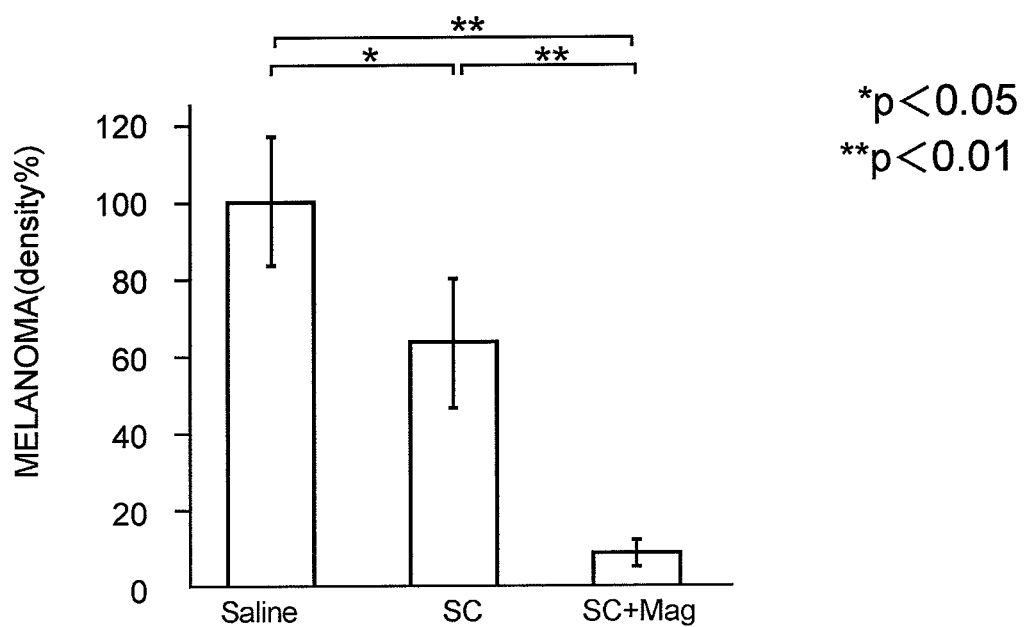
FIG. 12 is a characteristic diagram showing the effects of the Fe salen complex compound on melanomas.
Figure 13A:
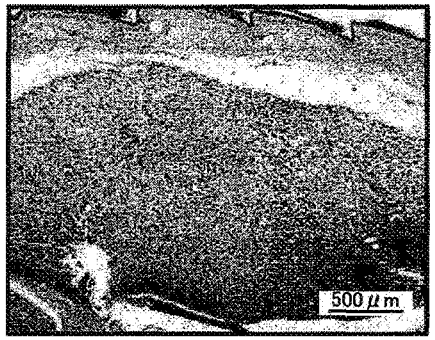
FIGS. 13A-13E are diagrams each showing the results of a histological examination of the Fe salen complex compound.
Figure 13B:
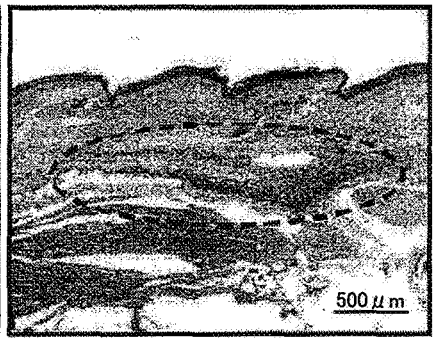
Figure 13C:
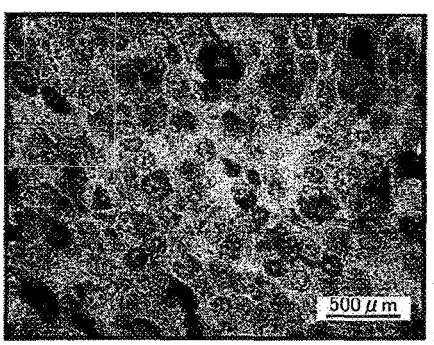
Figure 13D:
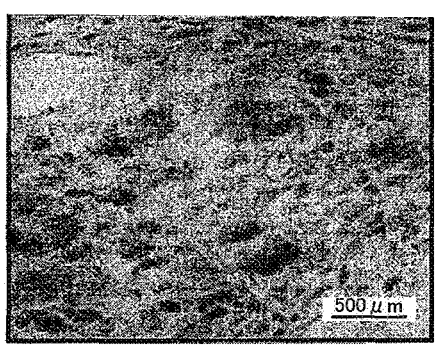
Figure 13E:
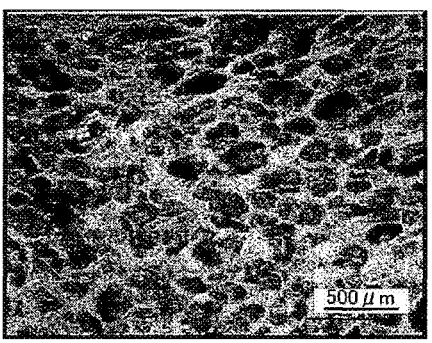

As shown in FIG. 12, the melanoma extension was greatest in the saline group (100±17.2%), in which saline, instead of the Fe salen complex compound, was injected. On the other hand, the melanoma extension modestly decreased (63.68±16.3%) in the SC group, into which the Fe salen complex compound was injected without the application of a magnetic force field. In contrast, most melanoma disappeared (9.05±3.42%) in the SC+Mag group, into which the Fe salen complex compound was injected and a magnet force field was applied as described above (n=7-10).

Incidentally, the same results were obtained for each of the Mn salen complex compound, the Cr salen complex compound, and the Co salen complex compound.

A histological examination was performed as shown in FIGS. 13A-13E by means of Hematoxylin-Eosin staining and immuno-histochemical staining with an anti-Ki-67 antibody and an anti-Cyclyn D1 antibody which are both tumor proliferation markers in tissue sections. As a result, the histological examination revealed that tumor expansion of melanoma diminished when the Fe salen complex compound was injected (SC); and the tumor expansion of melanoma mostly disappeared when the magnetic force field application was combined with the Fe salen complex compound.

Incidentally, the same results were obtained for each of the Mn salen complex compound, the Cr salen complex compound, and the Co salen complex compound.

Figure 14A:
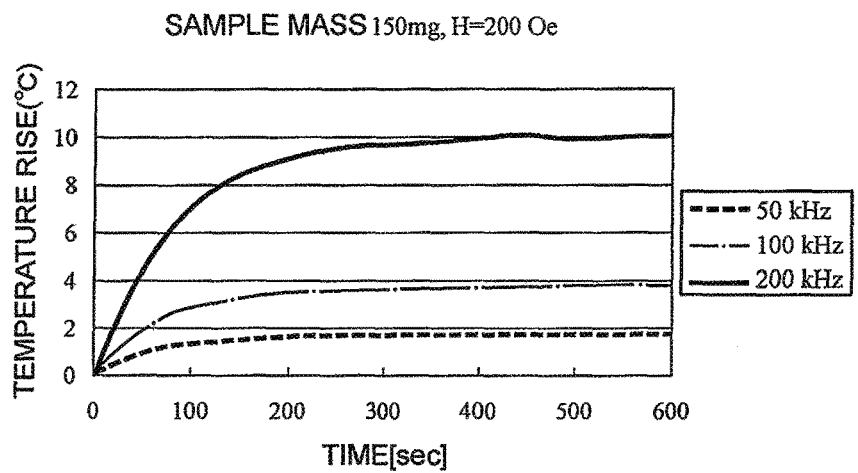
FIGS. 14A-14C are graphs each showing the relationship between magnetic field intensity or frequency of the Fe salen complex and a temperature rise.
Figure 14B:
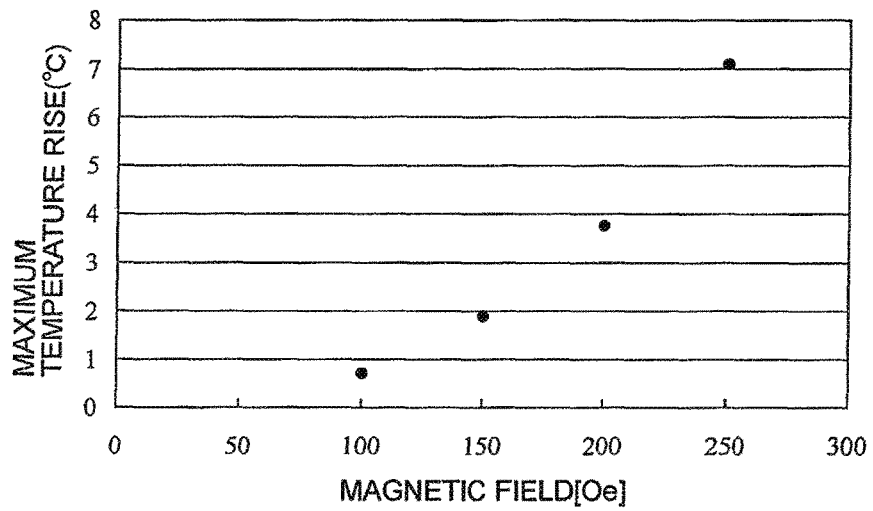
Figure 14C:
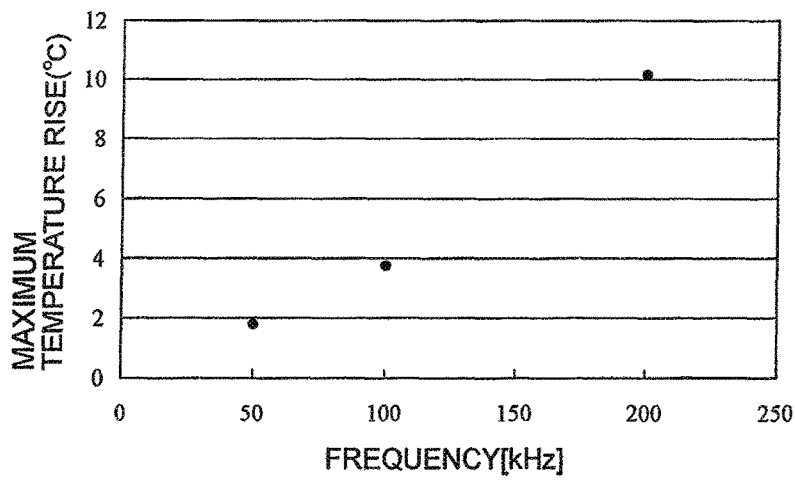

Furthermore, the application of an AC magnetic field with a magnetic field intensity of 200 Oe and a frequency of 50 kHz to 200 kHz to the drug (Fe salen complex compound; 9.25 mmol) increased the drug temperature by 2 degrees Celsius to 10 degrees Celsius (FIGS. 14A-14C). This confirmed that such temperature rise corresponds to the range from 39 degrees Celsius to 47 degrees Celsius as calculated in terms of temperature during administration to the living body and such temperature range is a temperature zone capable of killing cancer cells. Incidentally, FIG. 14A shows changes in temperatures with time when the AC magnetic field was applied to the drug; FIG. 14B shows the maximum temperature when only the magnetic field was changed while using a fixed frequency; and FIG. 14C shows the maximum temperature when only the frequency was changed while using a fixed magnetic field.

Incidentally, the same results were obtained for each of the Mn salen complex compound, the Cr salen complex compound, and the Co salen complex compound.

Example 7

The electron transfer of a compound which binds with the metal-salen complexes can be determined by first principles calculation. A system for realizing this computer simulation is equipped with well-known hardware resources as a computer, that is, memory, a computing device equipped with computing circuitry such as a CPU, and display means for outputting the computed results.

The memory includes data specifying existing organic compounds or three-dimensional structures, and software programs for performing computer simulation. The software program is capable of adding, modifying, and deleting side chains of each compound, cross linking certain side chains, calculating areas of high spin charge density, and determining the spin charge density for structures as a whole. For example, a commercially available program (Dmol3 by Accelrys) can be used as this program.

The user inputs the position where the side chains are to be added to a compound or selects one in which the side chains are modified or deleted, and uses a memory assisting program to designate on the computing device the location where cross linking should be formed. The computer receives the input values to calculate the spin charge density, and outputs the results on a display screen. The user can also add structural data on existing compounds to the computer system to obtain the spin charge density of existing compounds.

The charge transfer of a compound obtained by binding another compound to the metal salen complex can be determined by integrating the previously determined upward and downward spin charge density in three-dimensional space. The calculated results for charge transfer to e, b, k, h, or e, h of the aforementioned chemical formulas (I) and (II) are given in each of the following tables. With each table, a minus sign (−) indicates an increase of electrons and a plus sign (+) indicates a decrease of electrons.

[Table 1]

TABLE 1

| Metal Salen Complex (Chemical Formula I) | Compound To Be Combined | |
|---|---|---|
| Charge Transfer | Compound Name | Charge Transfer |
| −0.31 | Ibuprofen chemical formula (1) | +0.31 |
| −0.31 | Mefenamic acid chemical formula (2) | +0.31 |
| −0.32 | Pefloxacin chemical formula (3) | +0.32 |
| −0.31 | Gemfibrozil chemical formula (4) | +0.31 |
| −0.32 | Rhodamine chemical formula (5) | +0.32 |
| −0.35 | Estrogen chemical formula (6) | +0.35 |
| −0.35 | Estrogen chemical formula (7) | +0.35 |
| −0.34 | Taxol chemical formula (8) | +0.34 |
| −0.28 | Glycine chemical formula (9) | +0.28 |
| −0.28 | Alanine chemical formula (10) | +0.28 |
| −0.27 | Arginine chemical formula (11) | +0.27 |
| −0.27 | Asparagine chemical formula (12) | +0.27 |
| −0.25 | Asparatic acid chemical formula (13) | +0.25 |
| −0.26 | Cysteine chemical formula (114) | +0.26 |
| −0.26 | Glutamic acid chemical formula (15) | +0.26 |
| −0.25 | Histidine chemical formula (16) | +0.25 |
| −0.27 | Isoleucine chemical formula (17) | +0.27 |
| −0.26 | Leucine chemical formula (18) | +0.26 |
| −0.24 | Lysine chemical formula (19) | +0.24 |
| −0.28 | Methionine chemical formula (20) | +0.28 |
| −0.29 | Phenylalanine chemical formula (21) | +0.29 |
| −0.26 | Proline chemical formula (22) | +0.26 |
| −0.26 | Serine chemical formula (23) | +0.26 |
| −0.25 | Threonine chemical formula (24) | +0.25 |
| −0.28 | Tryptophan chemical formula (25) | +0.28 |
| −0.29 | Tyrosine chemical formula (26) | +0.29 |
| −0.25 | Valine chemical formula (27) | +0.25 |

[Table 2]

TABLE 2

| Metal Salen Complex (Chemical Formula I) | Compound To Be Combined | |
|---|---|---|
| Charge Transfer | Compound Name | Charge Transfer |
| −0.33 | Ifosfamide | +0.33 |
| −0.34 | Cyclophosphamide | +0.34 |
| −0.32 | Dacarbazine | +0.32 |
| −0.33 | Busulfan | +0.33 |
| −0.33 | Melphalan | +0.33 |
| −0.28 | Ranimustine | +0.28 |
| −0.30 | Estramustine sodium phosphate | +0.30 |
| −0.31 | Nimustine hydrochloride | +0.31 |
| −0.39 | Docetaxel hyderate | +0.39 |
| −0.38 | Vincristine sulfate | +0.38 |
| −0.38 | Vinblastine sulfate | +0.38 |
| −0.23 | Epirubicin hydrochloride | +0.23 |
| −0.33 | Vinorelbine ditartrate | +0.33 |
| −0.29 | Vindesine sulfate | +0.29 |
| −0.25 | Oxaliplatin | +0.25 |
| −0.22 | Carboplatin | +0.22 |
| −0.23 | Cisplatin | +0.23 |
| −0.24 | Nedaplatin | +0.24 |

[Table 3]

TABLE 3

| Metal Salen Complex (Chemical Formula I) | Compound To Be Combined | |
|---|---|---|
| Charge Transfer | Compound Name | Charge Transfer |
| −0.19 | Anastrozole | +0.19 |
| −0.18 | Afema | +0.18 |
| −0.28 | Exemestane | +0.28 |
| −0.13 | Toremifene citrate | +0.13 |
| −0.23 | Bicalutamide | +0.23 |
| −0.39 | Flutamide | +0.39 |
| −0.22 | Mepiotiostane | +0.22 |
| −0.30 | Estramustine sodium phosphate | +0.30 |
| −0.31 | Medroxyprogesterone acetate | +0.31 |
| −0.23 | Tamibarotene | +0.23 |
| −0.22 | Gefitinib | +0.22 |
| −0.24 | Tretinoin | +0.24 |
| −0.27 | Imatinib mesylate | +0.27 |
| −0.27 | Etoposide | +0.27 |
| −0.25 | Sobuzoxane | +0.25 |
| −0.22 | Irinotecan hydrochloride | +0.22 |
| −0.23 | Nogitecan hydrochloride | +0.23 |

[Table 4]

TABLE 4

| Metal Salen Complex (Chemical Formula I) | Compound To Be Combined | |
|---|---|---|
| Charge Transfer | Compound Name | Charge Transfer |
| −0.33 | Ubenimex | +0.33 |
| −0.31 | Sizofiran | +0.31 |
| −0.28 | Lenthinan | +0.28 |
| −0.33 | Ifosfamide | +0.33 |
| −0.34 | Cyclophosphamide | +0.34 |

TABLE 4-continued

| Metal Salen Complex (Chemical Formula I) | Compound To Be Combined | |
|---|---|---|
| Charge Transfer | Compound Name | Charge Transfer |
| −0.32 | Dacarbazine | +0.32 |
| −0.33 | Busulfan | +0.33 |
| −0.33 | Melphalan | +0.33 |
| −0.28 | Ranimusutine | +0.28 |
| −0.30 | Estramustine sodium phosphate | +0.30 |
| −0.31 | Nimustine hydrochloride | +0.31 |

[Table 5]

TABLE 5

| Metal Salen Complex (Chemical Formula I) | Compound To Be Combined | |
|---|---|---|
| Charge Transfer | Compound Name | Charge Transfer |
| −0.23 | Enocitabine chemical formula(3) | +0.23 |
| −0.24 | Capecitabine chemical formula(4) | +0.24 |
| −0.22 | Carmofur chemical formula(5) | +0.22 |
| −0.23 | Gimeracil chemical formula(6) | +0.23 |
| −0.33 | Oteracil potassium chemical formula(7) | +0.33 |
| −0.28 | Cytarabine chemical formula(8) | +0.28 |
| −0.30 | Cytarabine ocfosfate chemical formula(9) | +0.30 |
| −0.31 | Tegafur chemical formula(10) | +0.31 |
| −0.30 | Doxifluridine chemical formula(11) | +0.30 |
| −0.32 | Hydroxycarbamide chemical formula(12) | +0.32 |
| −0.33 | Fluorouracil chemical formula(13) | +0.33 |
| −0.35 | Mercaptopurine hydrate chemical formula(14) | +0.35 |
| −0.33 | Fludarabine phosphate chemical formula (15) | +0.33 |
| −0.34 | Gemcitabine hydrochloride chemical formula(16) | +0.34 |
| −0.33 | Actinomycin-D | +0.33 |
| −0.24 | Aclarubicin hydrochloride | +0.24 |
| −0.32 | Idarubicin hydrochloride | +0.32 |
| −0.23 | Epirubicin hydrochloride | +0.23 |
| −0.33 | Zinostatin stimalamer | +0.33 |
| −0.29 | Daunorubicin hydrochloride | +0.29 |
| −0.30 | Doxorubicin hydrochloride | +0.30 |
| −0.31 | Bleomycin hydrochloride | +0.31 |
| −0.19 | Peplomycin hydrochloride | +0.19 |
| −0.30 | Mitomycin C | +0.30 |
| −0.32 | Amrubicin hydrochloride | +0.32 |
| −0.33 | Pirarubicin hydrochloride | +0.33 |

[Table 6]

TABLE 6

| Metal Salen Complex (Formula II) | Compound To Be Combined | |
|---|---|---|
| Charge Transfer | Compound Name | Charge Transfer |
| −0.23 | Enocitabine | +0.23 |
| −0.24 | Capecitabine | +0.24 |
| −0.22 | Carmofur | +0.22 |
| −0.23 | Gimeracil | +0.23 |
| −0.33 | Oteracil potassium | +0.33 |
| −0.28 | Cytarabine | +0.28 |
| −0.30 | Cytarabine ocfosfate | +0.30 |
| −0.31 | Tegafur | +0.31 |
| −0.30 | Doxifluridine | +0.30 |

TABLE 6-continued

| Metal Salen Complex (Formula II) Charge Transfer | Compound To Be Combined Compound Name | Charge Transfer |
|---|---|---|
| −0.32 | Hydroxycarbamide | +0.32 |
| −0.33 | Fluorouracil | +0.33 |
| −0.35 | Mercaptopurine hydrate | +0.35 |
| −0.33 | Fludarabine phosphate | +0.33 |
| −0.34 | Gemcitabine hydrochloride | +0.34 |
| −0.33 | Actinomycin-D | +0.33 |
| −0.24 | Aclarubicin hydrochloride | +0.24 |
| −0.32 | Idarubicin hydrochloride | +0.32 |
| −0.23 | Epirubicin hydrochloride | +0.23 |
| −0.33 | Zinostatin stimalamer | +0.33 |
| −0.29 | Daunorubicin hydrochloride | +0.29 |
| −0.30 | Doxorubicin hydrochloride | +0.30 |
| −0.31 | Bleomycin hydrochloride | +0.31 |
| −0.19 | Peplomycin hydrochloride | +0.19 |
| −0.30 | Mitomycin C | +0.30 |
| −0.32 | Amrubicin hydrochloride | +0.32 |
| −0.33 | pirarubicin hydrochloride | +0.33 |

[Table 7]

TABLE 7

| Metal Salen Complex (Chemical Formula II) Charge Transfer | Compound To Be Combined Compound Name | Charge Transfer |
|---|---|---|
| −0.39 | Docetaxel hyderate | +0.39 |
| −0.38 | Vincristine sulfate | +0.38 |
| −0.38 | Vinblastine sulfate | +0.38 |
| −0.23 | Epirubicin hydrochloride | +0.23 |
| −0.33 | Vinorelbine ditartrate | +0.33 |
| −0.29 | Vindesine sulfate | +0.29 |
| −0.25 | Oxaliplatin | +0.25 |
| −0.22 | Carboplatin | +0.22 |
| −0.23 | Cisplatin | +0.23 |
| −0.24 | Nedaplatin | +0.24 |
| −0.19 | Anastrozole | +0.19 |
| −0.18 | Afema | +0.18 |
| −0.28 | Exemestane | +0.28 |
| −0.13 | Toremifene citrate | +0.13 |
| −0.23 | bicalutamide | +0.23 |
| −0.39 | Flutamide | +0.39 |
| −0.22 | Mepiotiostane | +0.22 |
| −0.30 | Estramustine sodium phosphate | +0.30 |
| −0.31 | Medroxyprogesterone acetate | +0.31 |

[Table 8]

TABLE 8

| Metal Salen Complex (Chemical Formula II) Charge Transfer | Compound To Be Combined Compound Name | Charge Transfer |
|---|---|---|
| −0.23 | Tamibarotene | +0.23 |
| −0.22 | Gefitinib | +0.22 |
| −0.24 | Tretinoin | +0.24 |
| −0.27 | Imatinib mesylate | +0.27 |
| −0.27 | Etoposide | +0.27 |
| −0.25 | Sobuzoxane | +0.25 |
| −0.22 | Irinotecan hydrochloride | +0.22 |
| −0.23 | Nogitecan hydrochloride | +0.23 |

TABLE 8-continued

| Metal Salen Complex (Chemical Formula II) Charge Transfer | Compound To Be Combined Compound Name | Charge Transfer |
|---|---|---|
| −0.33 | ubenimex | +0.33 |
| −0.31 | Sizofiran | +0.31 |
| −0.28 | Lenthinan | +0.28 |

[Table 9]

TABLE 9

| Metal Salen Complex (Chemical Formula I) Charge Transfer | Compound To Be Combined Compound Name | Charge Transfer |
|---|---|---|
| −0.22 | Lidocaine | +0.22 |
| −0.25 | Ethyl aminobenzoic acid | +0.25 |
| −0.25 | Oxybuprocaine | +0.25 |
| −0.24 | Oxethazaine | +0.24 |
| −0.23 | Dibucaine | +0.23 |
| −0.28 | Ethyl piperidinoacetylaminobenzoate | +0.28 |
| −0.25 | Procaine | +0.25 |
| −0.23 | Mepivacaine | +0.23 |
| −0.24 | p-butylaminobenzoyldiethylaminoethyl hydrochloride | +0.24 |
| −0.26 | Bupivacaine hydrochloride | +0.26 |
| −0.24 | Ropivacaine hydrochloride hydrate | +0.24 |
| −0.12 | Lidocaine | +0.12 |
| −0.15 | Ethyl aminobenzoic acid | +0.15 |
| −0.15 | Oxybuprocaine | +0.15 |
| −0.14 | Oxethazaine | +0.14 |
| −0.13 | Dibucaine | +0.13 |
| −0.18 | Ethyl piperidinoacetylaminobenzoate | +0.18 |
| −0.15 | Procaine | +0.15 |
| −0.13 | Mepivacaine | +0.13 |
| −0.14 | p-butylaminobenzoyldiethylaminoethyl hydrochloride | +0.14 |
| −0.16 | Bupivacaine hydrochloride | +0.16 |
| −0.14 | Ropivacaine hydrochloride hydrate | +0.14 |

[Table 10]

TABLE 10

| Metal Salen Complex (Chemical Formula I) Charge Transfer | Compound To Be Combined Compound Name | Charge Transfer |
|---|---|---|
| −0.32 | Leuplin chemical formula(3) | +0.32 |
| −0.35 | Methotrexate chemical formula(4) | +0.35 |
| −0.35 | Novanthrone chemical formula(5) | +0.35 |
| −0.34 | Photofrin chemical formula(6) | +0.34 |
| −0.33 | Photofrin chemical formula(7) | +0.33 |
| −0.28 | mylotarg | +0.28 |

Example 8

Figure 15:
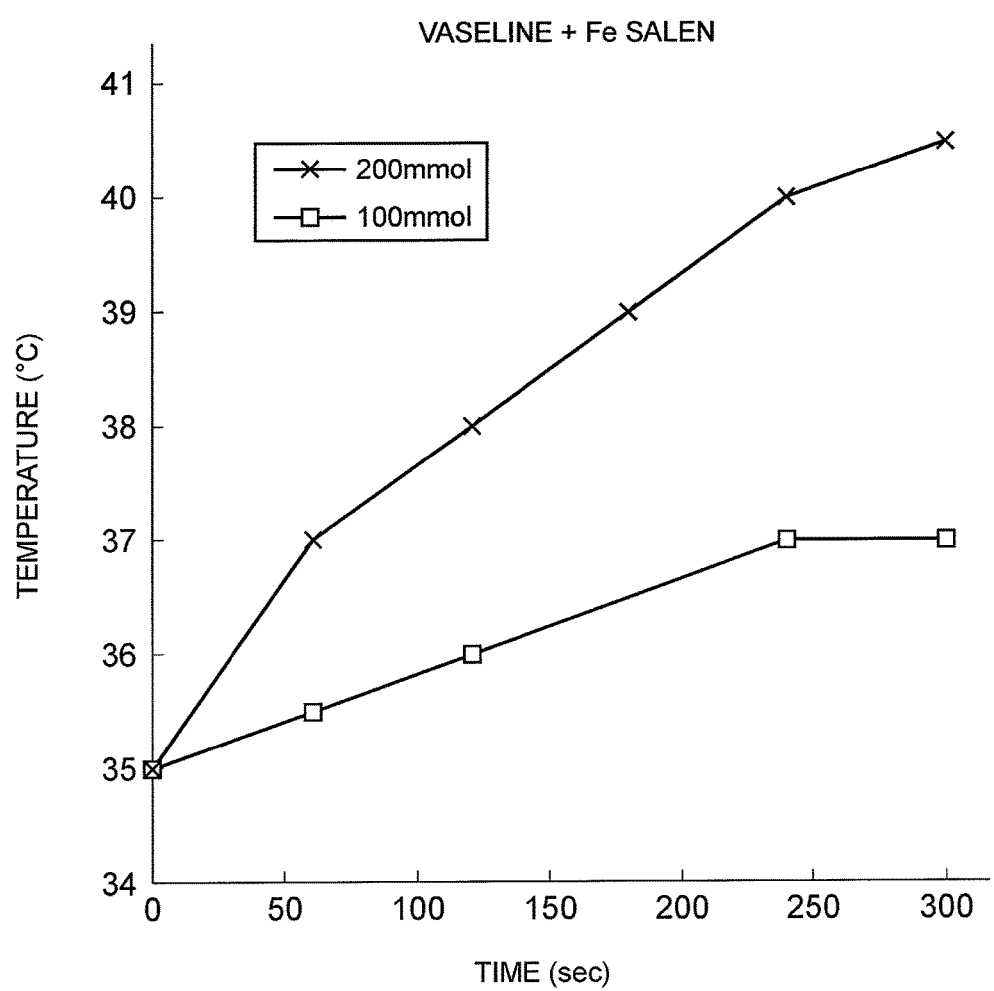
FIG. 15 is a graph showing the relationship between time and a temperature rise when an AC magnetic field is applied to an ointment in which Vaseline is used as a base and mixed with the Fe salen complex compound.

The aforementioned Fe salen complex compound was mixed with Vaseline, which is an adjuster for ointments, as a base at concentrations of 100 mmol and 200 mmol, respectively, to produce ointments. Then, the relationship between time and a temperature rise was measured by applying an AC magnetic field to these ointments under conditions of 258 A, 400 kHz, and 51.74 mT. The results are shown in FIG. 15. FIG. 15 shows that the temperature of the ointments at the concentrations of 100 mmol and 200 mmol immediately after the measurement (0 second) was 35 degrees Celsius and a temperature rise of approximately 5 degrees Celsius was observed for the ointment at the concentration of 200 mmol 300 seconds later.

Figure 16:
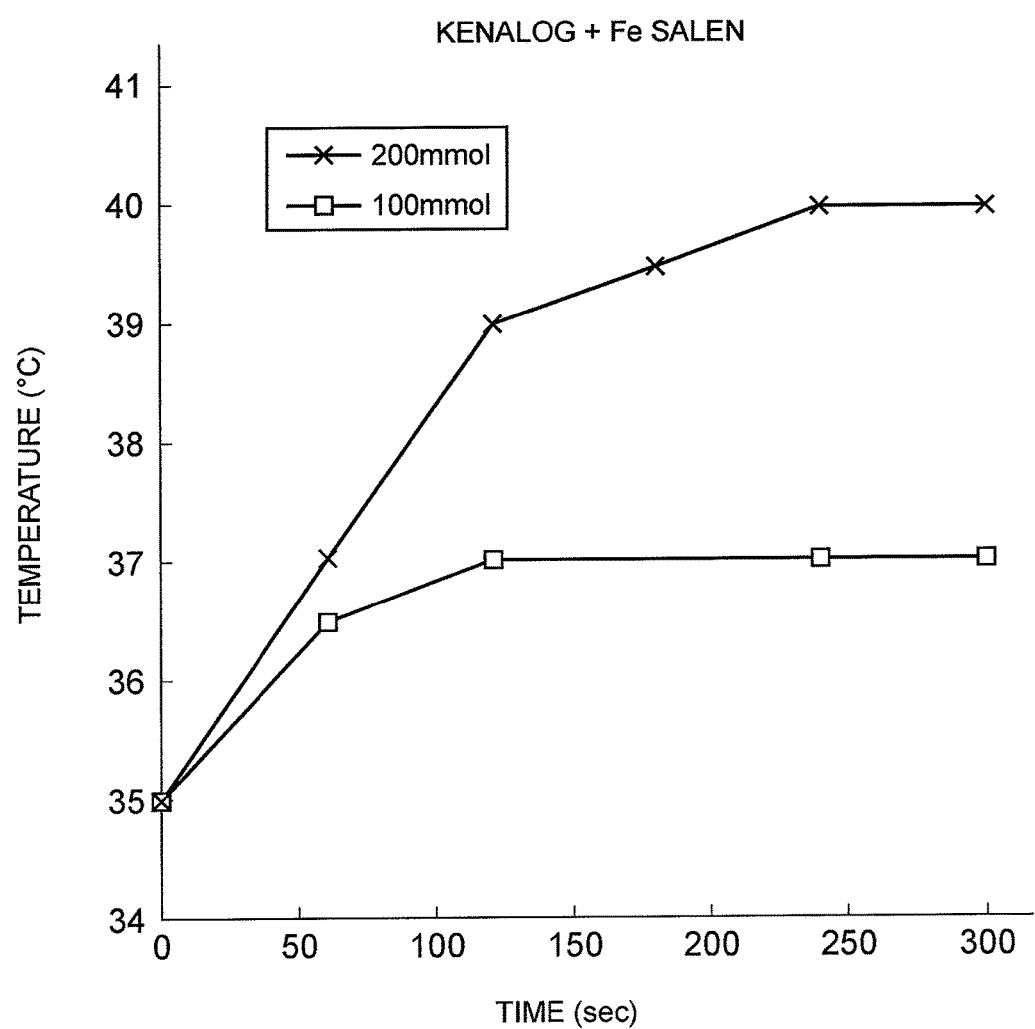
FIG. 16 is a graph showing the relationship between time and a temperature rise when the AC magnetic field is applied to an ointment in which Kenalog is used as a base and mixed with the Fe salen complex compound.

Then, the compound expressed by the aforementioned Formula (I) was mixed with Kenalog, which is an ointment for stomatitis, as a base at concentrations of 100 mmol and 200 mmol, respectively, to produce ointments. Then, the relationship between time and a temperature rise was measured by applying an AC magnetic field to these ointments under conditions of 258 A, 400 kHz, and 51.74 mT. The results are shown in FIG. 16. FIG. 16 shows that the temperature of the ointments at the concentrations of 100 mmol and 200 mmol immediately after the measurement (0 second) was 35 degrees Celsius and a temperature rise of approximately 5 degrees Celsius was observed for the ointment at the concentration of 200 mmol 300 seconds later.

Figure 17:
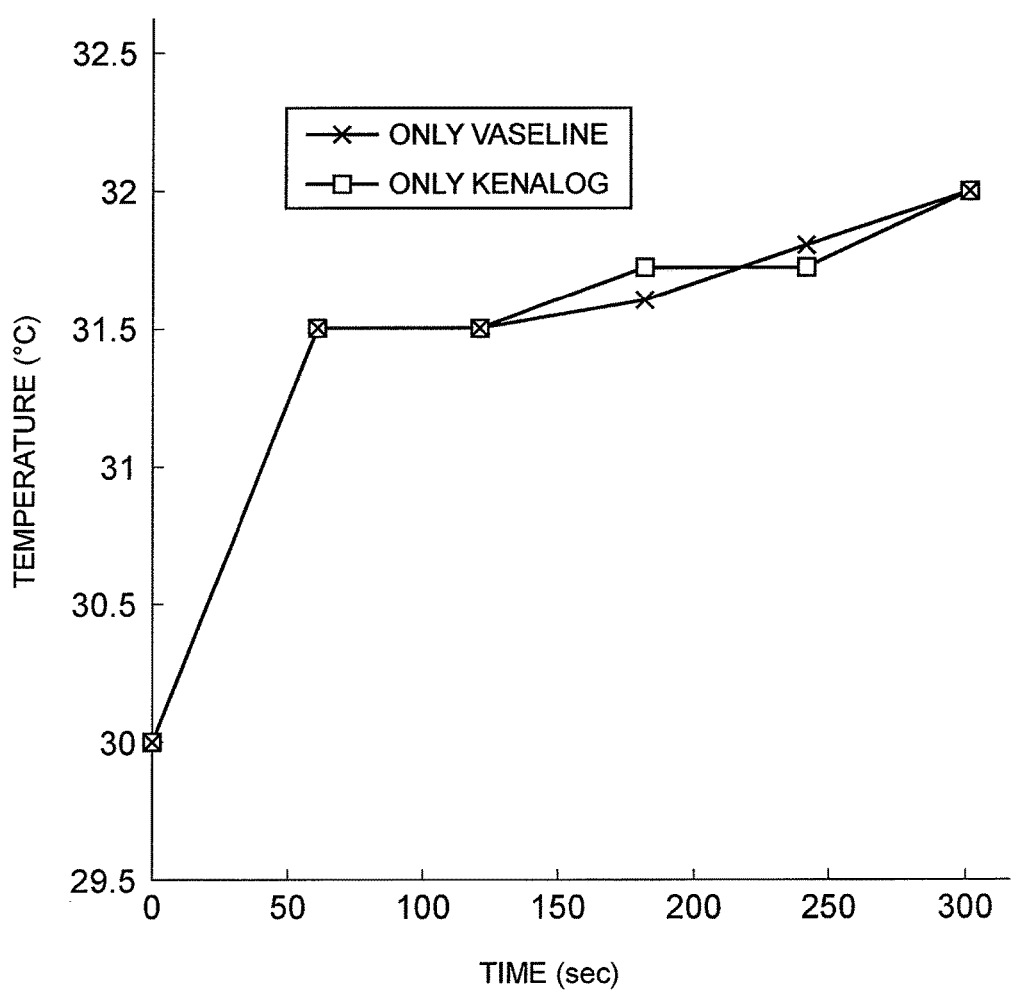
FIG. 17 is a graph showing the relationship between time and a temperature rise when an AC magnetic field is applied to only Vaseline and only Kenalog.

Next, as comparisons, the relationship between time and a temperature rise was measured by applying an AC magnetic field to each of 200 mg Vaseline and 200 mg Kenalog under conditions of 258 A, 400 kHz, and 51.74 mT. The results are shown in FIG. 17. FIG. 17 shows that the temperature of both Vaseline and Kenalog immediately after the measurement (0 second) was 30 degrees Celsius and a temperature rise even after application of the AC magnetic field for 300 seconds was less than 2 degrees Celsius.

The above results show that the temperature of the ointment, in which the metal-salen complex compound was mixed, immediately after the measurement is 5 degrees Celsius higher than only Vaseline and only Kenalog and is suited as an anti-tumor agent. Moreover, the ointment containing the metal-salen complex compound at the concentration of 200 mmol shows a significant temperature rise after the application of the AC magnetic field and is thereby more suited as an anti-tumor agent.

Incidentally, the same results were obtained for each of the Mn salen complex compound, the Cr salen complex compound, and the Co salen complex compound.

Furthermore, the same experiments as this embodiment were conducted for other metal-salen complex compounds according to the present invention, good results according to the above were obtained.

Example 9

Next, a diatomic Fe salen complex compound (CAS#14167-12-5; produced by Tokyo Chemical Industry Co., Ltd.) was dissolved in agarose to produce a 100 mmol solution, which was put in a test tube, thereby preparing a sample. A sample of pure water put in a test tube was also prepared as a comparison. Then, these samples were respectively exposed to medical near infrared radiation (wavelengths: 600 nm to 1600 nm) by TOKYO IKEN CO., LTD. by using Super Lizer PX Type I (output: 10 W). The relationship between time and a temperature rise is shown in FIG. 18.

Figure 18:
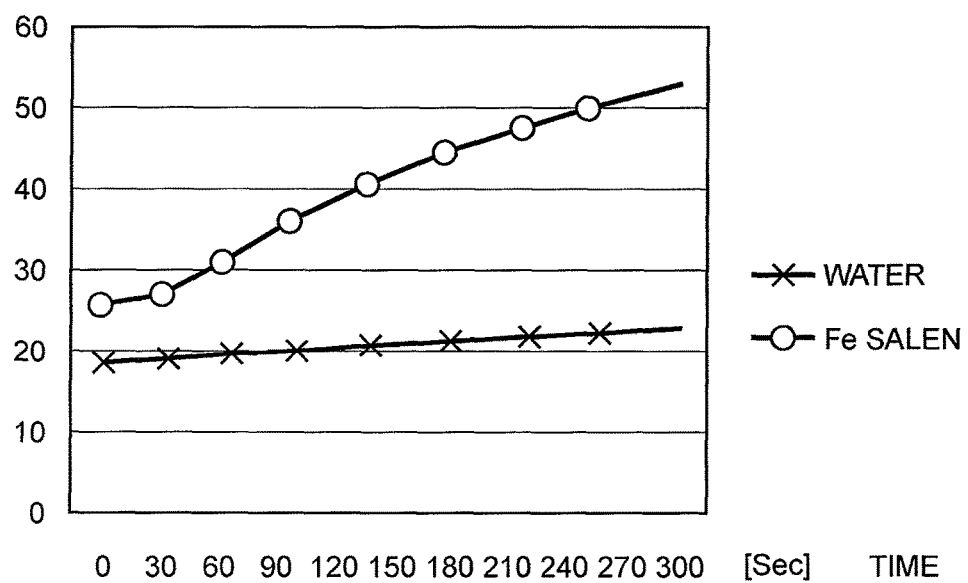
FIG. 18 is a graph showing the relationship between time and a temperature rise when a sample of a diatomic Fe salen complex compound dissolved in agarose is exposed to near infrared radiation.

FIG. 18 shows that the temperature of the sample containing the diatomic Fe salen complex compound immediately after the measurement (0 second) was 26 degrees Celsius and the temperature increased to approximately 53 degrees Celsius 300 seconds later. On the other hand, it is shown that the temperature of the sample containing the pure water immediately after the measurement (0 second) was approximately 19 degrees Celsius and its temperature 300 seconds later was approximately 23 degrees Celsius and did not increase so much.

The above results show that the temperature of the sample of the diatomic Fe salen complex compound dissolved in agarose increased significantly as a result of exposure to the near infrared radiation and, therefore, this sample is suited as an anti-tumor agent.

What is claimed is:
1. A method for treating a tongue cancer, the method comprising:
    administering an ointment to an cancer affected site of a tongue in a patient and applying a magnetic field to the cancer affected site to inhibit cancer cells of the tongue, wherein the ointment produced by mixing a self-magnetic metal-salen complex compound according to Formula (II) or (III) in a concentration of 200 mmol or higher with a base,

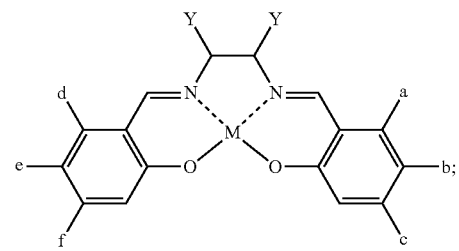

Formula (II)

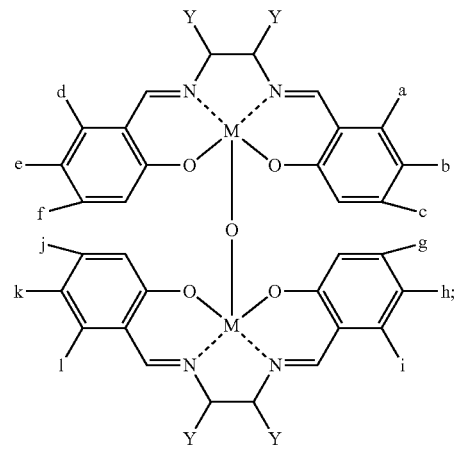

Formula (III)

wherein the M in the Formula (II) or (III) is Fe; and wherein each of the a to I and Y is independently hydrogen or (i) to (vi):

—CO₂Me, (i)

—CO(OCH₂CH₂)₂OCH₃, (ii)

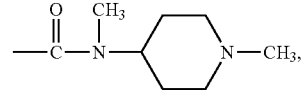

(iii)

(iv) one of —NHCOH, NH$_2$, —NHR$_1$, or NR$_1$R$_2$, wherein the R$_1$ and the R$_2$ are independently alkyl with carbon number from 1 to 6, (v) —R$_3$, wherein the R$_3$ is a therapeutic drug bound to the self-magnetic metal-salen complex compound via spin charge transfer, and (vi) halogen atoms selected from chlorine, bromine, or fluorine, wherein the applying a magnetic field to the cancer affected site reaches a magnetic field intensity thereby increasing a temperature of the self-magnetic metal-salen complex compound and inhibiting the cancer cells of the tongue by the increased temperature of the self-magnetic metal-salen complex compound, and wherein the magnetic field is an alternating magnetic field and the alternating magnetic field is applied to a surface of the cancer cells of the tongue.

2. The method of claim 1, wherein the R$_3$ is any one of compounds selected from gemfibrozil or paclitaxel.

3. The method of claim 1, wherein the ointment is an antineoplastic drug; and wherein the R$_3$ is fluorouracil or docetaxel hydrate.

4. The method of claim 1, wherein the ointment is an antineoplastic drug; and wherein the R$_3$ is methotrexate.

5. The method of any one of claims 1, 2, 3, and 4, wherein the self-magnetic metal-salen complex compound in an amount 0.01 wt % to 10 wt % is mixed with the base.

6. The method of any one of claims 1, 2, 3, and 4, wherein the base includes one of: Vaseline, Kenalog, liquid paraffin, polyethoxylated hydrogenated castor oil, macrogol, and gelled hygrocarbon.

* * * * *